(12) United States Patent
Tali et al.

(10) Patent No.: US 12,124,545 B2
(45) Date of Patent: Oct. 22, 2024

(54) COMMUNICATION NETWORK BASED NON-FUNGIBLE TOKEN CREATION PLATFORM WITH INTEGRATED CREATOR BIOMETRIC AUTHENTICATION

(71) Applicant: Taliware, Inc., San Diego, CA (US)

(72) Inventors: Tarik Tali, San Diego, CA (US); Hassan Zili, Tangier (MA); Abdelhak Tali, Tangier (MA)

(73) Assignee: TALIWARE, INC., San Diego, CA (US)

( * ) Notice: Subject to any disclaimer, the term of this patent is extended or adjusted under 35 U.S.C. 154(b) by 637 days.

(21) Appl. No.: 17/347,740

(22) Filed: Jun. 15, 2021

(65) Prior Publication Data
US 2021/0357489 A1 Nov. 18, 2021

Related U.S. Application Data

(63) Continuation-in-part of application No. 16/429,644, filed on Jun. 3, 2019, now Pat. No. 11,039,314, which
(Continued)

(51) Int. Cl.
*G06F 21/32* (2013.01)
*A61B 5/00* (2006.01)
(Continued)

(52) U.S. Cl.
CPC ............ *G06F 21/32* (2013.01); *A61B 5/117* (2013.01); *A61B 5/349* (2021.01); *A61B 5/681* (2013.01); *G01S 19/42* (2013.01); *G06F 16/2379* (2019.01); *G06F 21/35* (2013.01); *H04L 63/0861* (2013.01); *H04W 4/023* (2013.01); *H04W 12/065* (2021.01);
(Continued)

(58) Field of Classification Search
CPC .................................................. H04L 63/0861
See application file for complete search history.

(56) References Cited

U.S. PATENT DOCUMENTS 8,321,921 B1 * 11/2012 Ahmed ................ G06F 21/602
726/5
9,801,058 B2 10/2017 Tali
(Continued)

FOREIGN PATENT DOCUMENTS

WO 2019126471 6/2019

OTHER PUBLICATIONS

Master's Thesis of Lugovaya T.S. "Biometric human identification based on electrocardiogram." Faculty of Computing Technologies and Informatics, Electrotechnical University, Saint-Petersburg, Russian Federation, Jun. 2005.
(Continued)

*Primary Examiner* — Khang Do
(74) *Attorney, Agent, or Firm* — Blynn L. Shideler; Krisanne Shideler; BLK Law Group

(57) ABSTRACT

A geo-locations software management utility provides a method and system for passive authentication of an individual's geo-location via a communication network and for user authenticating images and video and social media content. Specifically a communication network based non-fungible token creation platform with integrated creator biometric authentication is disclosed.

11 Claims, 12 Drawing Sheets

Related U.S. Application Data is a continuation-in-part of application No. 15/790,328, filed on Oct. 23, 2017, now Pat. No. 10,708,778, which is a continuation-in-part of application No. 14/699,460, filed on Apr. 29, 2015, now Pat. No. 9,801,058.

(60) Provisional application No. 62/679,041, filed on Jun. 1, 2018, provisional application No. 61/985,693, filed on Apr. 29, 2014.

(51) Int. Cl.

| | | |
|---|---|---|
| *A61B 5/117* | (2016.01) | |
| *A61B 5/349* | (2021.01) | |
| *G01S 19/42* | (2010.01) | |
| *G06F 16/23* | (2019.01) | |
| *G06F 21/35* | (2013.01) | |
| *H04L 9/00* | (2022.01) | |
| *H04L 9/40* | (2022.01) | |
| *H04W 4/02* | (2018.01) | |
| *H04W 12/065* | (2021.01) | |
| *H04W 12/63* | (2021.01) | |
| *H04W 88/02* | (2009.01) | |

(52) U.S. Cl.
CPC ..... *H04W 12/63* (2021.01); *G06F 2221/2101* (2013.01); *G06F 2221/2111* (2013.01); *H04W 88/02* (2013.01)

(56) References Cited

U.S. PATENT DOCUMENTS

| | | | |
|---|---|---|---|
| 11,075,891 B1* | 7/2021 | Long | H04L 9/3213 |
| 11,514,423 B1* | 11/2022 | Kurani | G06F 3/04817 |
| 11,564,266 B1* | 1/2023 | Kahn | H04M 15/785 |
| 2002/0087264 A1 | 7/2002 | Hills | |
| 2003/0074568 A1* | 4/2003 | Kinsella | G06F 21/34 |
| | | | 713/186 |
| 2004/0015243 A1* | 1/2004 | Mercredi | G07C 9/37 |
| | | | 707/999.001 |
| 2005/0075116 A1 | 4/2005 | Laird | |
| 2008/0139114 A1 | 6/2008 | Ranganathan | |
| 2008/0200774 A1 | 8/2008 | Luo | |
| 2009/0270743 A1 | 10/2009 | Dugan | |
| 2010/0217099 A1 | 8/2010 | LeBoeuf | |
| 2012/0214442 A1* | 8/2012 | Crawford | G06F 21/316 |
| | | | 455/411 |
| 2012/0239479 A1 | 9/2012 | Amaro | |
| 2013/0030955 A1 | 1/2013 | David | |
| 2013/0133049 A1 | 5/2013 | Peirce | |
| 2013/0239185 A1* | 9/2013 | Orttung | H04L 63/08 |
| | | | 726/5 |
| 2013/0251216 A1* | 9/2013 | Smowton | G06V 40/67 |
| | | | 713/150 |
| 2013/0267253 A1 | 10/2013 | Case | |
| 2013/0290200 A1 | 10/2013 | Singhal | |
| 2014/0123325 A1 | 5/2014 | Jung | |
| 2014/0164249 A1 | 6/2014 | Guerrino | |
| 2014/0180566 A1 | 6/2014 | Malhotra | |
| 2014/0282877 A1* | 9/2014 | Mahaffey | H04W 12/33 |
| | | | 726/3 |
| 2014/0282915 A1* | 9/2014 | Tekwani | H04L 51/212 |
| | | | 726/4 |
| 2014/0289820 A1 | 9/2014 | Lindemann | |
| 2014/0318941 A1 | 10/2014 | Kilby | |
| 2015/0035643 A1 | 2/2015 | Kursun | |
| 2015/0065055 A1 | 3/2015 | Newham | |
| 2015/0077276 A1* | 3/2015 | Mitchell | G06Q 10/06 |
| | | | 340/995.1 |
| 2015/0081349 A1* | 3/2015 | Johndrow | G06Q 20/405 |
| | | | 705/5 |
| 2015/0105096 A1 | 4/2015 | Chowdhury | |
| 2015/0172920 A1* | 6/2015 | Ben Ayed | H04W 12/63 |
| | | | 713/172 |
| 2015/0277557 A1* | 10/2015 | Raffa | G06F 3/014 |
| | | | 345/156 |
| 2015/0305591 A1 | 10/2015 | Wolfe | |
| 2016/0044035 A1* | 2/2016 | Huang | H04L 41/0806 |
| | | | 726/4 |
| 2016/0164867 A1* | 6/2016 | Jung | H04W 12/068 |
| | | | 713/186 |
| 2016/0360354 A1 | 12/2016 | Rhee | |
| 2016/0364729 A1* | 12/2016 | Ruparelia | G06Q 20/1085 |
| 2017/0085563 A1* | 3/2017 | Royyuru | G06Q 20/12 |
| 2017/0195339 A1* | 7/2017 | Brown | H04W 4/80 |
| 2018/0039989 A1* | 2/2018 | Beye | G06Q 30/0601 |
| 2018/0049028 A1 | 2/2018 | Tali | |
| 2018/0060496 A1* | 3/2018 | Bulleit | H04L 9/0643 |
| 2018/0096175 A1* | 4/2018 | Schmeling | G06F 1/3206 |
| 2019/0312863 A1* | 10/2019 | Chow | H04L 9/0643 |
| 2020/0005284 A1* | 1/2020 | Vijayan | H04L 9/3247 |
| 2020/0175485 A1* | 6/2020 | Knock | G06Q 30/0621 |
| 2020/0342548 A1* | 10/2020 | Mazed | G06Q 30/0631 |
| 2021/0243027 A1* | 8/2021 | Gupta | G06F 21/32 |
| 2021/0266171 A1* | 8/2021 | Huang | H04L 9/3231 |
| 2021/0377052 A1* | 12/2021 | Brown | H04L 9/3239 |
| 2022/0182700 A1* | 6/2022 | Utile | G06Q 10/101 |
| 2022/0309491 A1* | 9/2022 | Shapiro | G06F 21/64 |
| 2022/0366762 A1* | 11/2022 | Nelson | G07F 17/3244 |

OTHER PUBLICATIONS

Y. Gahi, et al. "Biometric Identification System Based on Electrocardiogram Data" by University of Ontario Institute of Technology, 2000 Simcoe Street North, Oshawa, Ontario, Canada. L1H 7K4, 2008.

Abstract of: Odinaka, I and Preston M. Green in "ECG Biometric Recognition: A Comparative Analysis" Information Forensics and Security, IEEE Transactions on (vol. 7, Issue: 6 ) Biometrics Compendium, IEEE , pp. 1812-1824, 2012.

André Lourenço, Hugo Silva, and Ana Fred "Unveiling the Biometric Potential of Finger-Based ECG Signals" by, Computational Intelligence and Neuroscience vol. 2011 (2011), Article ID 720971.

\* cited by examiner

COMMUNICATION NETWORK BASED NON-FUNGIBLE TOKEN CREATION PLATFORM WITH INTEGRATED CREATOR BIOMETRIC AUTHENTICATION

RELATED APPLICATIONS

This application is a continuation in part of U.S. patent application Ser. No. 16/429,644 filed Jun. 3, 2019, titled Method and Apparatus for Passive Authentication of an Individual's Geo-Location via a Communication Network and for User Authenticating Images, Video, Social Media Check In and Social Media Content" which published Nov. 21, 2019 as publication number 2019/0357049 and which application and publication is incorporated herein by reference in its entirety.

U.S. patent application Ser. No. 16/429,644 claims priority to U.S. Patent Application Ser. No. 62/679,041 filed Jun. 1, 2018, titled Method and Apparatus for Passive Authentication of an Individual's Geo-Location via a Communication Network and for User Authenticating Images and Video and Social Media Check In and Social Media Content and Applications Using the Same" which application is incorporated herein by reference in its entirety.

U.S. patent application Ser. No. 16/429,644 is a continuation in part of U.S. patent application Ser. No. 15/790,328 filed Oct. 23, 2017 titled "Method and System for Authenticating an Individual's Geolocation Via a Communications Network and Applications Using the Same" which application is incorporated herein by reference in its entirety.

application Ser. No. 15/790,328 is a continuation in part of U.S. patent application Ser. No. 14/699,460 filed Apr. 29, 2015 and which published Jan. 21, 2016 as United States Patent Application Publication Number 2016-0021535 and which issued as U.S. Pat. No. 9,801,058 on Oct. 24, 2017, which publication and patent are incorporated herein by reference in their entireties.

U.S. patent application Ser. No. 14/699,460 claims priority to U.S. Patent Application Ser. No. 61/985,693 filed Apr. 29, 2014, titled "Method and System for Accessing, Acquiring, Storing and Managing each Individual's Geo-Location Position Data via a Communication Network Providing an Internet of Things Geo-Location Software Management Utility" which application is incorporated herein by reference in its entirety.

BACKGROUND INFORMATION

1. Field of the Invention

The present invention relates to a method and system for passive bio-authentication of an individual via a communication network and for user authenticating digital content in a non-fungible token.

2. Background Information

The term smartphone (or smartphone) is a mobile phone with an advanced mobile operating system which typically combines the features of a cell phone with those of other popular mobile devices, such as personal digital assistant (PDA), media players and GPS navigation units. Most smartphones have a touch screen user interface and can run third-party applications (apps), and are camera phones and audio recorders. Generally since at least 2012, smartphones have high-speed mobile broadband 4G LTE internet web browsing, motion sensors, and mobile payment mechanisms. In 2014, sales of smartphones worldwide topped 1.2 billion, which is almost a 30% increase from sales of 2013.

GPS, or global positioning satellite, is a satellite-based navigation system used to give exact location and time information anywhere on Earth. The system is maintained by the U.S. government and is accessible, free of charge, to anyone with a GPS receiver. Consumers have become increasingly reliant on GPS receivers for navigation while driving, as well as while biking and walking.

Originally, standalone GPS units, also known as personal navigation devices, were the only option available to consumers who wanted to take advantage of GPS technology. However, now that almost every current smartphone comes with a built-in GPS receiver, smartphones have largely replaced standalone units as consumers generally have found it is more convenient to just use their phones as navigation tools rather than bother with a separate standalone GPS unit. The smartphone GPS navigation apps are a subset of what can be considered broader geo-locations data management systems.

Smartphone GPS navigation apps gets frequent, automatic updates, meaning all the latest maps will always be on-hand and having the most current updates is invaluable when searching for points of interest along an unknown route, or when trying to re-route around heavy traffic. Using a smartphone as a GPS receiver taps into the idea of a smartphone as an all-in-one device. Many smartphone users always have their phones with them such that they will always have a GPS navigation tool on-hand. Smartphones are designed to be easily held in one hand, and thus are often the preferred choice for navigation while walking or biking. Smartphone GPS navigation apps not only have the ability to provide real-time traffic detection and avoidance, but can provide other services such as check gas prices. Additionally, the ability to call a business or tourist attraction to check hours and rates with a simple tap is one more advantage of using smartphone GPS navigation apps.

Smartphone GPS navigation apps allow for easy address entry. Smartphones allow users to look up a contact in their phone's address book and then navigate to that address without any additional typing. Also, addresses found via a smartphone Internet search or through another application can be sent directly to the GPS navigation app.

Current geo-locations data management systems such as the smartphone GPS based navigation apps are based on pinpointing the location of each individual's smartphone using the global positioning system (GPS) however, the geo-location position captured at any particular time does not confirm that the individual user (often owner) of the smartphone was also present at the time the geo-location position of their smartphone was captured. Furthermore, the data captured of the individual's location does not guarantee that this individual is the sole and unique owner of the smartphone used. It is one object of the present invention to address these deficiencies of the existing prior art.

NFTs

Non-fungible tokens or NFTs are cryptographic assets on blockchain with unique identification codes and metadata that distinguish them from each other. Alternatively an NFT may be defined as a unit of data stored on a digital ledger, called a blockchain that certifies a digital asset to be unique and therefore not interchangeable. Unlike cryptocurrencies, they cannot be traded or exchanged at equivalency. This differs from fungible tokens like cryptocurrencies, which are identical to each other and, therefore, can be used as a medium for commercial transactions. The distinct construction of each NFT has been recognized has having great potential for several use cases including digital artwork. NFTs involving digital art generally do not store the file on the blockchain due to its size. The token functions in a way more similar to a certificate of ownership, with a web address pointing to the piece of art in question. Further, because they are based on blockchains, NFTs can also be used to remove intermediaries and connect artists with audiences or for identity management. NFTs can remove intermediaries, simplify transactions, and create new markets. NFTs can often also contain ownership details for easy identification and transfer between token holders. Owners can also add metadata or attributes pertaining to the asset in NFTs. For example, artists can sign their digital artwork with their own signature in the metadata.

NFTs evolved from the ERC-721 standard. Developed by some of the same people responsible for the ERC-20 smart contract, ERC-721 defines the minimum interface—ownership details, security, and metadata—required for exchange and distribution of gaming tokens. The ERC-1155 standard takes the concept further by reducing the transaction and storage costs required for NFTs and batching multiple types of non-fungible tokens into a single contract. The FLOW blockchain which uses proof of stake consensus model supports NFTs, for example NBA Top Shot is run on the FLOW blockchain. Tezos is a blockchain network that operates on proof of stake and supports the sale of NFT art.

One of the most famous use case for NFTs is that of cryptokitties. Launched in November 2017, cryptokitties are digital representations of cats with unique identifications on an Ethereum blockchain. Each kitty is unique and has a price in ether. They reproduce among themselves and produce new offspring, which have different attributes and valuations as compared to their parents. Within a few short weeks of being launched, cryptokitties racked up a fan base that spent $20 million worth of ether purchasing, feeding, and nurturing them. Some enthusiasts even spent upwards of $100,000 on the effort. Cryptokitties plans to switch from Ethereum to FLOW in the future.

Non-fungible tokens are an evolution over the relatively simple concept of cryptocurrencies. As another example, digital artwork entitled "Everydays—The First 5000 Days", by artist Mike Winkelmann, also known as Beeple, sold for US$69.3 million in 2021. The purchase resulted in the third-highest auction price achieved for a living artist, after Jeff Koons and David Hockney. Another Beeple piece entitled "Crossroad", consisting of a 10-second video showing animated pedestrians walking past a figure of Donald J. Trump, sold for US$6.6 million at Nifty Gateway, an online cryptocurrency marketplace for digital art.

Blockchain and the technology enabling the network have given the opportunity for musicians to tokenize and publish their work as non-fungible tokens. This has extended the list of options for musicians and artists alike to monetize and profit from their music as well as other content surrounding the themes of the music and the artist's public image. Additionally, NFTs have provided the opportunity for artists and touring musicians to recuperate lost income due to the 2020 COVID-19 pandemic which resulted in music industry revenues to fall nearly 85%. Similar to limited edition merchandise or a physical copy of an artist's work, NFTs allow more avenues for fans to connect with and support their favorite bands or artists. NFTs were extremely influential to the music industry within 2021 where many artists across all genres explored the usage of NFTs in their streams of revenue. In February 2021 alone, NFTs reportedly generated around $25 million within the music industry leading to increased ventures in the medium by more artists. On Feb. 28, 2021, electronic dance musician 3LAU sold a collection of 33 NFTs for a total of $11.7 million to commemorate the three-year anniversary of his Ultraviolet album. On Mar. 3, 2021, rock band Kings of Leon became the first to announce the release of a new album, When You See Yourself, in the form of an NFT. The NFT went on to generate a reported $2 million in sales, in which more than quarter of the revenue was donated to charity benefiting live entertainment workers. Later the same month, American rapper Lil Pump partnered with the NFT platform Sweet, to release a special NFT collection. Record producer Mike Dean united with artist Shepard Fairey to release their NFT collection OBEY 4:22 on Apr. 23, 2021. The release serves as the follow up to Dean's 2020 album 4:20. The NFT collection was only available during a 15-minute window in which all of the music of 4:22 was performed and improvised through a series of live streams through Twitch and Instagram live. On Apr. 25, 2021, rapper and producer Eminem released original instrumental beats and other collectables as an NFT collection, titled ShadyCon. In early May 2021, the estate of rapper XXXTentacion announced that it would release five songs and previously never before seen footage from his 2017 tour as an NFT collection.

In a Mar. 27, 2021 Saturday Night Live episode, cast members satirized this growing NFT niche with a comedy skit on NFTs, which skit was later sold in the form of an NFT for $365,000 on Apr. 6, 2021. Even the patent world is not immune from the commercialization opportunities of NFTs. In May 2021, UC Berkeley announced that it would be auctioning NFTs for the patent disclosure documents (invention disclosure forms filled out by university inventors) for two Nobel Prize-winning inventions: CRISPR-Cas9 gene editing and cancer immunotherapy. The university will continue to own the patents for these inventions, as the NFTs relates only to the university patent disclosure forms.

The individualized or unique aspect and authenticating protocols of NFTs make them well suited for digital artwork as outlined above, however there is still a need to provide authentication of authorship at the point of the NFT creation and to have this accomplished in an automated fashion.

SUMMARY OF THE INVENTION

This invention is directed to a cost effective, efficient, method and system for passively authenticating, accessing, acquiring, storing and managing each individual's geo-location position data via a communication networks. More precisely this invention is directed to a cost effective, efficient, method and system for authenticating, accessing, acquiring, storing and managing each individual's geo-location position data via a communication networks and private blockchain networks, the storing of the data on the private blockchain network, and the rendering of the stored data on the private blockchain available to be consumed as goods and services on the blockchain.

One aspect of the present invention provides a cellular communication network based method of non-fungible token creation with integrated creator biometric authentication comprising the steps of: a) providing the individual with a smartphone having a global positioning system (GPS) receiving unit associated with the communications network; b) providing the individual with a passive biometric user identification technology coupled to the smartphone; c) obtaining via the communications network the geo-location of the smartphone utilizing the GPS receiving unit; d) identifying the individual with the passive biometric user identification technology by passively obtaining biometric characteristics that are unique to each human via the communications network; e) identifying digital data files on the smartphone; f) verifying via the communications network the biometric user identification technology is within a preset proximity to the smartphone; g) authenticating the individual via the communications network and creating authentication data associated with the authenticated individual and associated with the digital data files; and h) recording on a blockchain the authentication data of the individual and authentication data associated with the digital data files.

The communication network based method of one aspect of the present invention provides wherein the biometric user identification technology utilizes the individual's electrocardiogram as a biometric characteristic that is unique to each human and wherein the biometric user identification technology utilizes a wristband worn by the individual and wherein the wristband is coupled to the smartphone, and wherein the step of verifying via the communications network the biometric user identification technology is within a preset proximity to the smartphone to authenticate the individual's mobile geo-location anywhere within a geographic scope of the communications network of the smartphone.

The communication network based method of one aspect of the invention provides wherein the associated blockchain implements a token issuance schema and wherein the digital data files include at least one of audio, video, and image files, and wherein the step of recording the individual's authentication data includes the steps of recording the individual's authentication data off of the associated blockchain and recording hashes of the recorded data on the associated blockchain. The communication network based method of one aspect of the invention may provide wherein the step of recording the individual's authentication data off of the associated blockchain is on the cloud. The communication network based method of one aspect of the invention may provide wherein the associated blockchain implements a token issuance schema and wherein the digital data files include at least one of audio, video, and image files.

The communication network based method of one aspect of the invention provides wherein the method includes authenticating multiple individuals, wherein each individual is provided with an individual smartphone and at least some individuals use a smartphone worn on a wrist, and wherein the method includes the step of incorporating defined restricted areas for each individual. The communication network based method may further provide wherein the defined restricted areas for each user is configured to be able to be varied by time.

The communication network based method of one aspect of the invention further includes the step of integrating the authentication data of the individual user with location based social networks data as proof-of-presence of the individual user in the location based social network data.

The communication network based method of the present invention may provide wherein the passively obtained biometric characteristics are obtained with a single user click.

One aspect of the present invention provides a communication network based non-fungible token creation platform with integrated creator biometric authentication comprising: a) a smartphone for a platform user having a global positioning system (GPS) receiving unit associated with the communications network; b) a passive biometric user identification technology coupled to the smartphone associated with the platform user; c) means for obtaining via the communications network the geo-location of the smartphone utilizing the GPS receiving unit; d) means for identifying the individual platform user with the passive biometric user identification technology by passively obtaining biometric characteristics that are unique to each human via the communications network; e) means for identifying digital data files on the smartphone; f) means for verifying via the communications network the biometric user identification technology is within a preset proximity to the smartphone; g) means for authenticating the individual via the communications network and creating authentication data associated with the authenticated individual and associated with the digital data files; and h) means for recording on a blockchain the authentication data of the individual and authentication data associated with the digital data files.

The method of the invention using the cellular communication network of one aspect of the invention may further include recording the individual's authenticated geo-locations for at least a period of time, wherein during recording of the individual's authenticated geo-locations, the method may include recording any periods when the individual's geo-location cannot be authenticated. Periods when the individual's geo-location cannot be authenticated include when the biometric characteristics obtained by the biometric user identification technology fail to identify the user and when the biometric user identification technology is not within a preset proximity to the smartphone.

The method of one aspect of the invention may further include cross-checking the authenticated individual's geo-location with location based check-in data from location based platforms to further validate as proof-of-presence the geo-location data of the individual's presence at a certain location. The method may further include identifying any anomalous results between the authenticated individual's geo-location and the location based check-in data from location based platforms.

The method of one aspect of the present invention may further include marking recordings, such as pictures, videos or audio recordings, taken with the individual smartphone with the geo-location where the image was taken, the time the image was taken, and the authenticated geo-location data of the individual when and where the image was taken. The method will allow for authentication of any image, video, audio recording and/or sensor reading recorded by the smartphone to verify the individual making the record via the smartphone and their location, if needed. The biometric user identification technology in this context may be implemented as a fingerprint scan on the smartphone, and this technology may be made "passive" by implementing the fingerprint scan simultaneous with the implementing of the recording on the smartphone.

The method of one aspect of the invention further includes limiting access to at least some of the smartphone applications, e.g. banking applications, to the individual as verified by the biometric user identification technology. The method may further provide wherein the step of limiting access to at least some of the smartphone applications to the individual as verified by the biometric user identification technology includes limited access to at least some of the smartphone applications when the individual and the smartphone are within pre-defined geo-locations. For example, a bank ATM may utilize and interact with the smartphone of the individual to quickly and safely access a proper individual's account and the bank ATM may further verify the identity of the individual both with the biometric technology and by the presence of the phone and individual at the designated ATM geo-location, thereby passively providing a high level of security. The biometric user identification technology in this context may be implemented as a fingerprint scan on the smartphone, and this technology may be made "passive" by implementing the fingerprint scan simultaneous with the opening of and/or performing a designated function within an associated banking application on the smartphone.

The method of the present invention provides wherein the individual owner of the smartphone interacts with Internet-Of-Things devices. The biometric user identification technology in this context may be implemented as a fingerprint scan on the smartphone, and this technology may be made "passive" by implementing the fingerprint scan simultaneous with the opening of and/or performing a designated function within an associated ITO device application on the smartphone.

One aspect of this invention is passive geoauthentication system using a phones camera system coupled with fingerprint scanning to have the finger scan be activated with the same motion/user action as taking the picture. This is not just for passive geoauthentication, but can be implemented for passively authenticating images and video (or audio or other sensor activations) taken with the phone outside of geoauthentication, namely creating NFTs. In practice some smartphones already allow the user to unlock the phone with stored fingerprint biometrics. The present invention implements this technology into the camera and/or video application on the phone as the method of activating the camera for still pictures or video recording. Thus when the user selects the camera application on the phone the activation to take a picture or begin recording will be to press a finger (or thumb) onto the screen wherein the phone can scan the finger and verify the user's biometric and simultaneously operate the camera for taking an image or recording a video. This biometric can be used to authenticate the geoposition of the user as identified in this application. Additionally the image or video recording can be authenticated or verified and appropriately marked regarding the verified author, regardless of whether the users geolocation is also identified on the image or recording. This can be very valuable for providing verified authorship to images and video recordings. It should be apparent that the same concept is applicable to audio recordings as well wherein the user actuates the recording and authenticates the user with a biometric, namely finger scan.

The system and method may be described as relating to a comprehensive geo-location software management utility and includes a wristband equipped with a digital ECG wireless transmitter, a secured user-to-smartphone unique cardiac rhythms identification access system, a cellular network, a storage network, a database and online software as a service application. The present invention system and method secures that the both the individual, e.g. the user of the smartphone, and the associated smartphone were both present at same geo-location position of the smartphone through global positioning system (GPS) when the data was captured and logged-in in to the database by the geo-location software management utility. Furthermore, the present system and method secures that the smartphone used when the data was captured indeed belongs to the individual at the time the geo-location position GPS of the smartphone was captured and logged-in.

The method of the invention implementing a private blockchain network, A Dapp, smart contracts, tokens, a distributed file sharing called swarm of one aspect of the invention may further include recording the individual's authenticated geo-locations for at least a period of time on the private blockchain, wherein during recording of the individual's authenticated geo-locations, the method may include recording any periods when the individual's geo-location cannot be authenticated. Periods when the individual's geo-location cannot be authenticated include when the biometric characteristics obtained by the biometric user identification technology fail to identify the user and when the biometric user identification technology is not within a preset proximity to the smartphone.

The method for one aspect of the invention may further include integrating and writing on the blockchain the authenticated individual's geo-location with location based social networks data (e.g., FACEBOOK®, FOURSQUARE®, etc) as proof-of-presence of the individual in the location based social network data.

The system and method may be described as relating to a comprehensive geo-location software management utility and includes a wristband equipped with a digital ECG wireless transmitter, a secured user-to-smartphone unique cardiac rhythms identification access system, a cellular network, a storage network, a private blockchain database network, A Dapp, smart contracts, tokens, a distributed file sharing called swarm, an online software as a service application. The present invention system and method secures that the both the individual, e.g, the owner of the smartphone, and the associated smartphone were both present at same geo-location position of the smartphone through global positioning system (GPS) when the data was captured and logged-in in to the private blockchain database by the blockchain geo-location smart contract software management utility. Furthermore, the present system and method secures that the smartphone used when the data was captured and written to the blockchain indeed belongs to the individual at the time the geo-location position GPS of the smartphone was captured and logged-in.

These and other aspects of the present invention will be clarified in the description of the preferred embodiment of the present invention described below in connection with the attached figures in which like reference numerals represent like elements throughout.

BRIEF DESCRIPTION OF THE PREFERRED EMBODIMENTS

Figure 1:
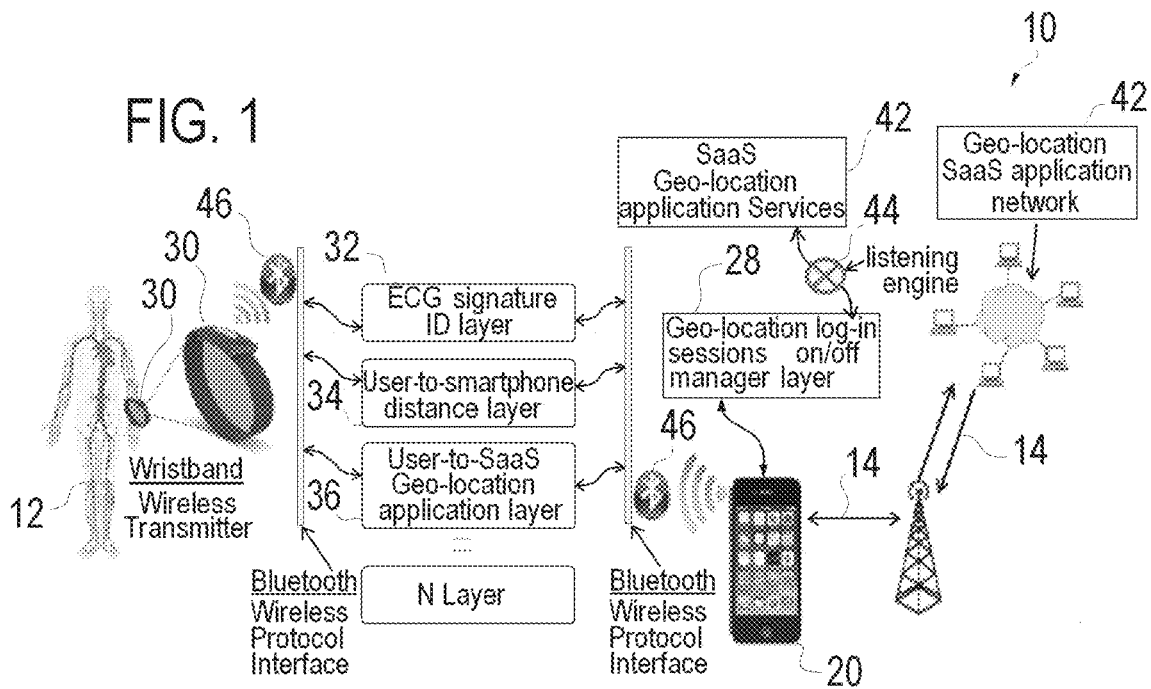
FIG. 1 is a schematic diagram of a system for authenticating an individual's geo-location via a communication network in accordance with one aspect of the present invention.

As discussed above the present invention relates to user geo-location software and also to an on the blockchain geo-locations software management utility. Specifically the present invention provides a method and system for storing an individual's geo-location via a communication network, and may further include incorporation into a private blockchain network, and applications using the same. The details and operation of private blockchain networks are known in general in the art. The revolutionary aspects of blockchain technology is commonly being touted, but they still suffer from the "garbage in-garbage out" problem. The application of, or incorporation of, user geo-location software of the present invention with a blockchain network is further detailed in U.S. Publication 2020/0329018 and WO/2019-126471, which publications are incorporated herein by reference, and this helps verify user inputs into a blockchain network.

The blockchain networks should be briefly discussed herein. As an example, a bank or credit card processing company may wish to validate that a bank transaction that is actually taking place is indeed being carried by the person holder of the credit card. The present invention systems and method in this case scenario shows how the communications network, the private blockchain and the token software management issues a token access for the bank or associated company to use and points to the private blockchain where the individual of concern's geo-location certified data by the individual's heart signature is located. Once the validation of the individual's geo-location takes place the bank or processing company then can approve or deny the transaction. Thus the token will be used as virtual ticket or access pass to a private blockchain to exploit an authenticated geolocation service.

Smart contracts allow anonymous parties to enter into binding agreements, with each participant having full transparency on the deal being made. Value can be transferred between accounts or held in escrow inside the smart contract itself. As the contract is just code, the application is only limited by the developer's imagination. Thus the present invention may be utilized to help create, execute and/or defines a smart contract on the private blockchain network between the banks, the courts, the lawyers and other entities for an exchange of bitcoin for an access pass to exploit our authenticated geolocation services verified using heart rate wristband biometrics (or other biometrics) tethering the individual to their smartphones as proof-of-presence of their location at a point of time.

As well known, blockchains can be used for a wide variety of applications, such as tracking ownership or the provenance of documents, digital assets, physical assets or voting rights and in our present invention to store the individual's heart rate signature along with the individual's geo-location verified by the wristband tethered to the smartphone. Blockchain technology was popularized by the Bitcoin digital currency system, but, essentially, a blockchain is just a special kind of database. So the blockchain system has been designed to use nodes agreement to order transactions and prevent fraud described. As detailed below one aspect of the present invention provides a cellular communication network based method of non-fungible token creation with integrated creator biometric authentication Geoposition Authentication This invention is directed in some aspects to a cost effective, efficient, system 10 for authenticating accessing, acquiring, storing and managing the geo-location position data of each individual 12 via a communication network 14 associated with the individual's smartphone 20, which includes a GPS receiving unit. The system 10 uses a biometric user identification technology, preferably passive biometric user identification technology, and in one preferred embodiment a continuous and passive wristband based electrocardiogram 30. This system as detailed below provides the integrated creator biometric authentication cellular communication network based method of non-fungible token creation.

There are many types of biometric user identification technologies, but there are several types that are most commonly used. Biometric user identification is basically the recognition of human characteristics that are unique to each human, which can include fingerprints, hand geometry, retinal scanning, iris scanning, facial recognition, vein pattern, voice recognition, DNA, electrocardiograms, and more.

FINGERPRINT TECHNOLOGY—Fingerprint identification techniques fall into two major categories-Automated Fingerprint Identification Systems (AFIS) and fingerprint recognition systems. AFIS is typically restricted to law-enforcement use. Fingerprint recognition derives a unique template from the attributes of the fingerprint without storing the image itself or even allowing for its reconstruction. Fingerprint recognition for identification acquires the initial image through live scan of the finger by direct contact with a reader device that can also check for validating attributes such as temperature and pulse. Since the finger actually touches the scanning device, the surface can become oily and cloudy after repeated use and reduce the sensitivity and reliability of optical scanners. Solid state sensors overcome this and other technical hurdles because the coated silicon chip itself is the sensor. Solid state devices use electrical capacitance to sense the ridges of the fingerprint and create a compact digital image, so they are less sensitive to dirt and oils. Fingerprint recognition is generally considered reliable and readers are in commercial use, and some vendors have actively marketed readers as part of Local Area Network login schemes.

HAND GEOMETRY—The essence of hand geometry is the comparative dimensions of fingers and the locations of joints. One of the earliest automated biometric systems, INDENTIMAT, installed at the Shearson-Hamill investment bank on Wall St. during the late 60s, used hand geometry and stayed in production for almost twenty years. Some systems perform simple, two-dimensional measurements of the palm of the hand. Others attempt to construct a simple three-dimensional image from which to extract template characteristics. In one of the most popular descendants of the INDENTIMAT system, a small digital camera captures top and side images of the hand. Reference marks on a platen allow calibration of the image to improve the precision of matching.

RETINAL SCAN—Retinal recognition creates an "eye signature" from the vascular configuration of the retina, an extremely consistent and reliable attribute with the advantage of being protected inside the eye itself. An image of the retina is captured by having the individual look through a lens at an alignment target. Diseases or injuries that would interfere with the retina are comparatively rare in the general population, so the attribute normally remains both consistent and consistently available.

IRIS SCANNING—Iris scanning is less intrusive than retinal recognition because the iris is easily visible from several feet away. Responses of the iris to changes in light can provide secondary verification that the iris presented as a biometric factor is genuine. A balance of light, focus, resolution, and contrast can be necessary (depending upon the scanner) to extract the attributes or minutiae from the localized image. It is noteworthy that while the iris seems to be consistent throughout adulthood, it does vary somewhat up to adolescence.

FACIAL RECOGNITION—Face recognition technology has made substantial advances in the last few years. Acquisition for biometric identification purposes generally requires the individual's face to be presented to a video camera. A facial thermo-gram works much like face recognition except that the image is captured by way of an infrared camera, and the heat signature of the face is used to create the biometric template used for matching.

VEIN PATTERN—Hand vein recognition attempts to distinguish individuals by measuring the differences in subcutaneous features of the hand using infrared imaging. Like face recognition, it must deal with the extra issues of three-dimensional space and the orientation of the hand. Like retinal scanning, it relies on the pattern of the veins in the hand to build a template with which to attempt matches against templates stored in a database. The use of infrared imaging offers some of the same advantages as hand geometry over fingerprint recognition in manufacturing or shop-floor applications where hands may not be clean enough to scan properly using a conventional video or capacitance technique.

VOICE RECOGNITION—Voice recognition techniques are generally categorized according to two approaches-Automatic Speaker Verification (ASV) and Automatic Speaker Identification (ASI). Speaker verification uses voice as the authenticating attribute in a two-factor scenario. Speaker identification attempts to use voice to identify who an individual actually is. Voice recognition distinguishes an individual by matching particular voice traits against templates stored in a database. Voice systems must be trained to the individual's voice at enrollment time, and more than one enrollment session is often necessary. Feature extraction typically measures formants or sound characteristics unique to each person's vocal tract. The pattern matching algorithms used in voice recognition are similar to those used in face recognition.

DNA—DNA is the gold standard of biometric user identification, but presently there is no efficient scanner to provide practical real time results.

ELECTROCARDIOGRAMS—Electrocardiograms (ECG also called EKG—from Greek with "kardia" meaning heart) are records of electrical currents generated by the beating heart, and have been found to be a distinctive identifying human characteristic, since ECG waveforms and other properties of the ECG depend on the anatomic features of the human heart and body. It has been suggested that the use ECG for biometric identification is supported by the fact that the physiological and geometrical differences of the heart in different individuals display certain identifiable uniqueness in their ECG signals. See "Biometric human identification based on electrocardiogram." [Master's thesis of Lugovaya T. S.] Faculty of Computing Technologies and Informatics, Electrotechnical University, Saint-Petersburg, Russian Federation, June 2005. See also Biometric human identification based on electrocardiogram. Nemirko A. P., Lugovaya T. S. Proc. XII-th Russian Conference on Mathematical Methods of Pattern Recognition, Moscow, MAKS Press, 2005, pp. 387-390. See also Biometric Identification System Based on Electrocardiogram Data by Y. Gahi, et al University of Ontario Institute of Technology, 2000 Simcoe Street North, Oshawa, Ontario, Canada. L1H 7K4, 2008. For a systematic review and discussion of the current associated methods and the techniques that have been applied to the use of the electrocardiogram for biometric recognition see ECG Biometric Recognition: A Comparative Analysis by Odinaka, I and Preston M. Green in Information Forensics and Security, IEEE Transactions on (Volume: 7, Issue: 6) Biometrics Compendium, IEEE, Pgs. 1812-1824, 2012.

Although traditional ECGs have been through the chest of the user other application sites are known. For example, a finger based ECG has been disclosed and implemented, see Unveiling the Biometric Potential of Finger-Based ECG Signals by André Lourenço, Hugo Silva, and Ana Fred, Computational Intelligence and Neuroscience Volume 2011 (2011), Article ID 720971. The present invention prefers to utilize a wrist based ECG acquisition unit 30 as described below. A suitable ECG device is the biometric ECG bracelet manufactured by Bionym, although others have proposed such devices. The wrist worn ECG 30 is one preferred biometric identification technology because it is passive and monitors effectively continuously. It is passive as it does not require the user to take a scanning step like placing a finger or hand or face within a scanning perimeter, the user merely needs to put on the bracelet 30 (or other implementing device). The unit 30 is continuous as it can regularly perform an ECG at defined intervals (e.g. every 10 seconds) in an automated fashion.

In certain implementations the finger scan technology can be made "passive", namely where the finger scan is combined with actuation of some other activity on the smartphone, thus "eliminating" the extra scanning step. For example, the if the video camera on the smartphone 20 is actuated (with user authentication to be added to the recording) with a user's finger pressed onto the screen which simultaneously i) operates the camera to take an image or begin a recording and ii) performs a biometric finger scan; then in this context the biometric identification is deemed passive because there is no added scanning step because it has been integrated into another action already required by the user. This technology represents one version of a single click NFT creation protocol detailed herein.

The alternative biometric user identification technologies discussed above could be implemented into the system with the addition of an associated scanner (which scanners are, outside of DNA, already commercially available), however the alternative biometric user identification technologies will generally require an active authentication step by the user (allowing a retinal scan, iris scan, hand scan or facial scan, speaking for a voice sample) and can limit the automatic authentication further than is available with the continuous passive monitoring of the wrist worn ECG 30.

As a broad overview, integrated creator biometric authentication component of the present invention provides a system 10 for authenticating a geo-location of an individual 12 via a communication network 14 comprising a) a smartphone 20 having a GPS receiving unit, generally 28, associated with a communications network 14, wherein the system 10 is configured to obtain via the communications network 14 the geo-location of the smartphone 20 utilizing the GPS receiving unit 28; and b) a biometric user identification technology in the form of ECG bracelet 30 worn by the individual configured to obtain biometric characteristics that are unique to each human, wherein the system 10 is configured to identify, generally at 32, the individual 12 with the biometric user identification technology of ECG bracelet 30 and to verify the biometric user identification technology of ECG bracelet 30 is within a preset proximity, generally at 34, to the smartphone 20 to authenticate the individual's geo-location, generally at 36.

A broad overview of the integrated creator biometric authentication of the present invention is that the invention provides a method for authenticating the geo-location of an individual 12 via a communication network 14 comprising the steps of: a) providing an individual 12 with a smartphone 20 having a GPS receiving unit (generally 28) associated with a communications network 14; b) providing the individual 12 with a biometric user identification technology, such as ECG bracelet 30; c) obtaining via the communications network 14 the geo-location of the smartphone 20 utilizing the GPS receiving unit 28; d) identifying at 32 the individual 12 with the biometric user identification technology formed by ECG bracelet 30 by obtaining biometric characteristics that are unique to each human; and e) verifying at 34 the biometric user identification technology of ECG bracelet 30 is within a preset proximity to the smartphone 12 to authenticate the individual's geo-location at 36.

Authenticating an individual's geo-location via a cellular communication network 14 of one aspect of the invention may further include recording, possibly at a remote service provider 42, the individual's authenticated geo-locations for at least a period of time, wherein during recording of the individual's authenticated geo-locations, the method may include recording any periods when the individual's geo-location cannot be authenticated. Periods when the individual's geo-location cannot be authenticated include when the biometric characteristics obtained by the biometric user identification technology fail to identify the individual and when the biometric user identification technology is not within a preset proximity to the smartphone 20.

Authenticating an individual's geo-location via a communication network 14 of one aspect of the invention provides wherein system 10 includes incorporating user defined restricted areas for the individual. The restricted areas could be areas in which the individual must remain and operate (e.g., authorized work zones, house arrest limitations, school boundaries), or it could be areas that the individual is prevented from entering (e.g., restricted/high security areas, restraining order limitations) or both. The system may include sending a warning message to the individual when the individual is approaching a boundary of the user defined restricted area. As noted above, "approaching a boundary" is broadly defined in this application as it is intended to encompass both coming close to a restricted area or leaving a defined work area. Further it should be understood that the user defined areas may vary by time and/or by individual.

Authenticating an individual's geo-location via a communication network 14 of one aspect of the invention may provide wherein a single user, such as a service provider 42 is authenticating multiple individual's geo-locations. Authenticating an individual's geo-location via a communication network 14 of one aspect of the invention may further include a system 10 which integrates the authenticated individual's geo-location with location based social networks data (e.g., FACEBOOK®, FOURSQUARE®, etc.) as proof-of-presence of the individual in the location based social network data, and for managing and/or authenticating images and videos and recordings posted by the individual user 12.

Authenticating an individual's geo-location via a communication network 14 of one aspect of the invention may further include cross-checking the authenticated individual's geo-location with location based check-in data from location based platforms to further validate as proof-of-presence the geo-location data of the individual's presence at a certain location. The system 10 may further include identifying any anomalous results between the authenticated individual's geo-location and the location based check-in data from location based platforms.

The system 10 for authenticating an individual's geo-location via a communication network 14 of one aspect of the present invention may further include marking recordings, such as pictures, videos or audio recordings, taken with the individual smartphone 20 with the geo-location where the image was taken, the time the image was taken, and the authenticated geo-location data of the individual 12 when and where the recording (image or the like) was taken. The system 10 will allow for authentication of any image, video, audio recording and/or sensor reading recorded by the smartphone 20 to verify the location and individual 12 making the record via the smartphone 20. In this implementation of the present invention a passive biometric user identification technology may be a fingerprint scan on the user smartphone 20, wherein the scan is integrated into the video or image or recording actuation on the smartphone 20. Several commercial smartphones already incorporate such scanning for user access (AKA "unlocking the phone") and thus the present invention merely integrates this scan with the signal to begin recording or take an image. The recording can have the authenticating information incorporated therewith. This can be used for managing social media as well. With the authentication the recording (image or video or the like) can be linked to an individuals desired social media and uploaded with a quick swipe of the finger. It is anticipated that a single phone 20 may have several authorized users, with each user being able to seamlessly couple and upload authenticated images to their respective social media accounts.

Authenticating an individual's geo-location via a communication network 14 of one aspect of the invention may further include limiting access to at least some of the smartphone 20 applications, e.g. banking applications, to the individual 12 as verified by the biometric user identification technology of the ECG bracelet 30 or other biometric user identification technology. The system 10 may further provide wherein the limiting access to at least some of the smartphone applications to the individual 12 as verified by the biometric user identification technology includes limited access to at least some of the smartphone applications when the individual 12 and the smartphone 20 are within pre-defined geo-locations. For example, a bank ATM may utilize and interact with the smartphone 20 of the individual 12 to quickly and safely access a proper individual's account and the bank ATM may further verify the identity of the individual 12 both with the biometric technology of the ECG bracelet 30 or other biometric technology and by the presence of the phone 20 and individual 12 at the pre-designated ATM geo-location, thereby passively providing a high level of security. In this application the bracelet 30 and a fingerprint scan can yield passive authentication. The fingerprint scan can be made passive where it is integrated into another function such as actuating an App on the phone 20 or conducting a transaction on the phone 20 within such and application.

Authenticating an individual's geo-location via a communication network 14 with the system 10 provides wherein the individual owner of the smartphone interacts with Internet-Of-Things devices 61. All of these aspects will be described further below.

The system 10 and method may be described as relating to a comprehensive web3.0 software utility, an Internet of Things (IoT) geo-locations software management utility via a communication network 14 and includes a ECG wristband 30 (with Bluetooth transmitter) that an individual 12 wears on his/her wrist, a secured user-to-smartphone identification access management system, a cellular network 14, a storage network, a database and an online software as a service application provider 42. More simply, the present invention deals with securing that both the individual 12 and the smartphone 20 are always present at the same geo-location at the time the geo-location of the smartphone 20 via (GPS) position is captured and logged-in by the geo-location software into the database via a communications network 14 as schematically illustrated in FIG. 1.

In order to determine that both the individual 12 (sometimes who may be the owner of the smartphone 20) and the smartphone 20 are, were both present at the same geo-location position, the individual must wear a wrist band 30 that is equipped with a wireless data transmitter so that the geo-location software management utility can manage the individual's presence with their smartphone 20. Further if the wristband 30 is worn by an individual 12 at all times the geo-location software management utility 42 can capture and store data via a communications network 14 of individual's traveled path history. The ECG wristband 30 is equipped with heart signal transmitter and obtains unique cardiac rhythm signals for each individual 12 which can be used to verify at 32 the identity of the individual 12 according to pre-existing ECG signals associated with the individual. The particular algorithms used for matching ECG signals are known to those in the biometric art. In addition to verifying the geo-position of the individual 12 the ECG wristband 30 of system 10 may be used to give the individual 12 a wireless, non-contact auto access to their smartphone 20 or selected apps thereon. In other words the wearing of the wristband 30 may be required for the individual 12 to access and use select apps of the phone 20.

Practically the present invention includes a geo-location software application the individual 12 (or distinct system 10 user such as employer, oversight official or the like) needs to download and install in the smartphone 20. Once the geo-location software application is installed in the individual's smartphone 30, a listening engine 44 process is launched and runs as a hidden process in the smartphone 20 background. At the same time, the geo-location software that is now running as an application on the individual's phone 20 alerts the geo-software networks 42 letting them know that a new individual 12 will be using the geo-location software management services and to create a database to store this new and unique individual's data.

Now that geo-location software management utility is installed in the individual's smartphone 20, and the listening engine 44 is running as a process in the background the auto-detect process to secure that both the individual 12 and their smartphone 20 are both present at the same location for proof-of-presence can start.

As noted above, the system 10 integrates an ECG wristband 30 to be worn by an individual 12 at all times. The wristband 30 is equipped with heart rhythm signal wireless transmitter 46 and generates unique cardiac rhythms for each individual. Like a fingerprint (and other identifying biomarkers), each individual's ECG heart rhythms are unique to each individual 12. The present invention system 10 uses the individual cardiac rhythms of the ECG from wristband 30 to authenticate the individual 12's identity, allowing individuals 12 to wirelessly authenticate and gain access to select apps on their smartphone 20. This log-in state data is stored in a register in the smartphone 20 memory and is to be used by the software management listening engine 44.

The geo-software management listening engine 44 runs as a process in the smartphone 20 background and is always looking at detecting and validating two conditional states: 1] The log-in state, that the individual 12 has securely gained access, and is now logged-in to their smartphone 20. 2] That the distance or the tolerated threshold set to be maintained at all times between the worn wristband 30 by the individual 12 and their smartphone 20 is maintained and is valid. These two states validation are essential and must be valid in order for the geo-location software management to start or stop capturing and storing the individual's authenticated geo-location position.

The listening engine 44 continuously reads the logged-in state register data that is previously stored in the smartphone 20 memory when the individual 12 has gained access to their smartphone 20 (because the band 30 has verified the identity of the individual with the biometric). If the log-in state is true, then the listening engine 44 only needs verify if the distance between the wristband 30 and the smartphone 20 is within the assigned threshold. If the distance measured between the wristband 30 and the smartphone 20 is with-in the threshold, then the present system 10 authenticates that the individual 12 and the smartphone 20 are both present at the same geo-location position.

The present invention system 10 is a geo-location software management utility 42 which can capture the individual's geo-location position and stores the data in a database online (at 42) which can be accessed online at a later time for viewing and printing. This geo-location software application must be downloaded and installed by the individuals 12 in their smartphone 20. When the geo-location software application is installed in the individual's smartphone 20, the geo-location software application alerts the geo-location software online service network 42 via a communications network 14 letting them know that an individual 12 has installed the software application and wants the geo-location services to begin capturing and storing their geo-location position. The geo-location software management utility contains a software sub-routine process called the listening engine 44 and runs automatically and continually without the intervention or need of input of the individual 12. This listening engine 44 runs as a process in the background of the smartphone 20 and monitors if the user/individual 12 is still logged-in and has access to their smartphone 20, which operation is schematically shown in the figures.

The system 10 and associated method solves one issue that can be called a proof-of-presence of the individual at a certain location at a certain time. The geo-location software as a service application provider 42 not only captures and stores data online via a communications network 14 of the location of the individual's smartphone 12 using GPS but also secures that the individual 12 who is the owner/registered user of the cell phone 20 is also present when the smartphone's geo-position was captured and stored. In this invention, the data captured and stored provides a verified history of the locations of the individual's traveled path. Individuals (or the system 10 user which may be an employer or the like) can access, on demand, through their smartphones 20 their geo-locations data history and be able to view or print a hard copy of their geo-location's whereabouts for any specific day and time in the past.

Figure 7:
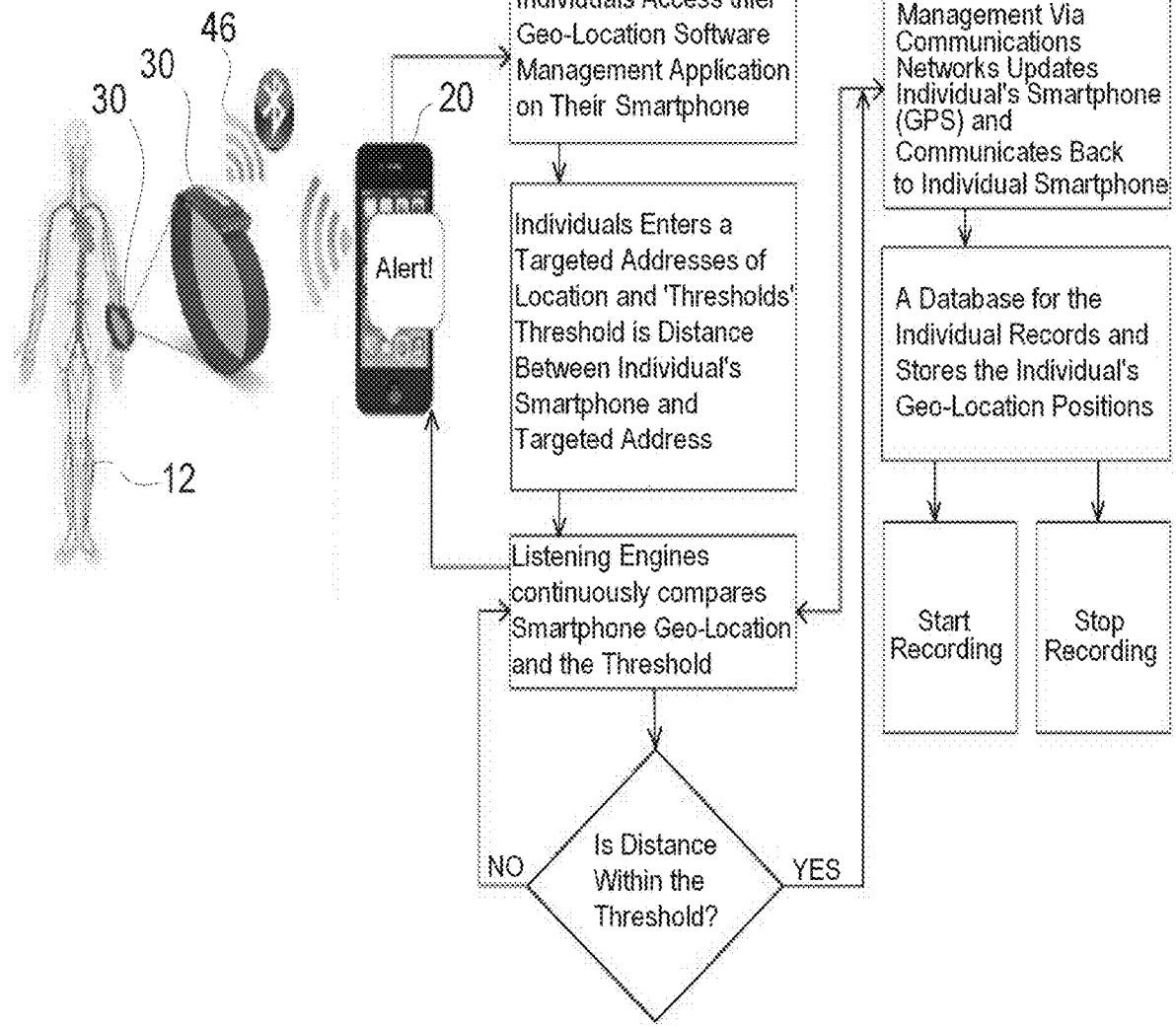
FIG. 7 is a schematic diagram of a process for communication of Smartphone to address geo-position identification and warning in accordance with one aspect of the system of FIG. 1.

The present system 10 and associated method allows individuals 12 to access the geo-location software utility 28 that is running on their smartphones 20 to turn on the smartphone-to-address distance warning. Here the individual 12 (or system 10 user for given individuals 12) can setup a comfortable distance between their smartphone geo-location position and an address they want the geo-location utility to alert them they are approaching when on a traveled path. Individuals 12 can select an address, using multi-touch over a map on their smartphone 20, or by keying the address in the geo-location database, and set a range or distance threshold, as shown in FIG. 7. As the individual 12 is traveling, the geo-location software management continually measures the distance between the address stored in the database and the individual's smartphone (GPS) location. A real-time warning is issued, when the smartphone-to-address has entered the threshold distance. Individuals 12 can target multiple address locations, and set threshold distances to all using the geo-location software management service.

Figure 8:
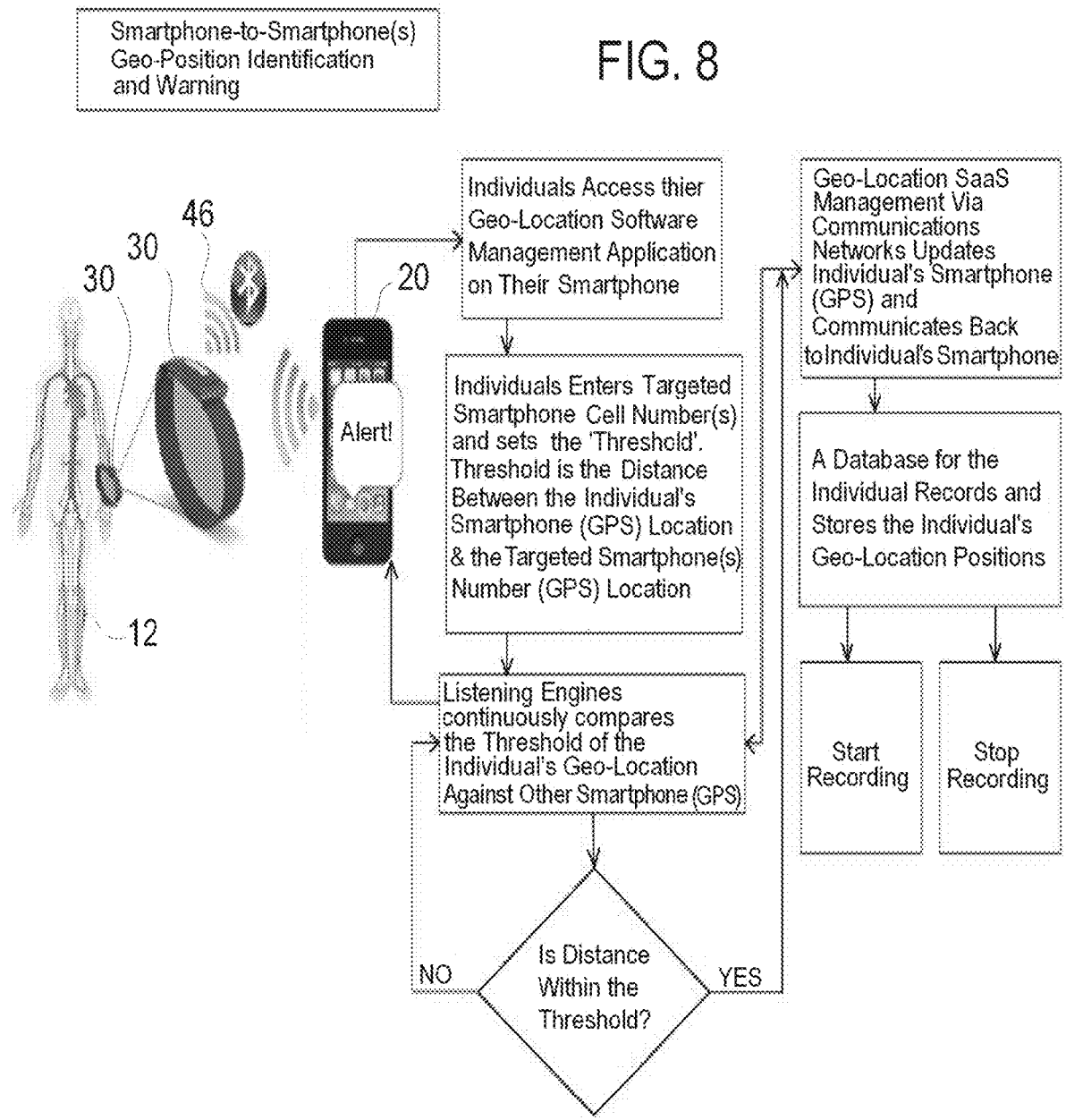
FIG. 8 is a schematic diagram of a process for communication of Smartphone to smartphone(s) geo-position identification and warning in accordance with one aspect of the system of FIG. 1.

Furthermore, the present system 10 allows individuals to access the geo-location software service that is running on their smartphones 20 and activate smartphone-to-smartphone(s) threshold alert options as shown in FIG. 8. Individuals 12 can select other smartphones numbers as targets they wish to maintain a certain geo-position distance away from. As the individual 12 is traveling, the geo-location software management continually measures the distance between the smartphone's (GPS) target number(s) stored in the database and the individual's own smartphone (GPS) geo-location, assuming the target phone has GPS and is accessible to the system 10. A real-time warning is issued, when the pre-set target threshold is violated. Individuals can target multiple smartphones, and set thresholds to all using the geo-location software management service.

Figure 9:
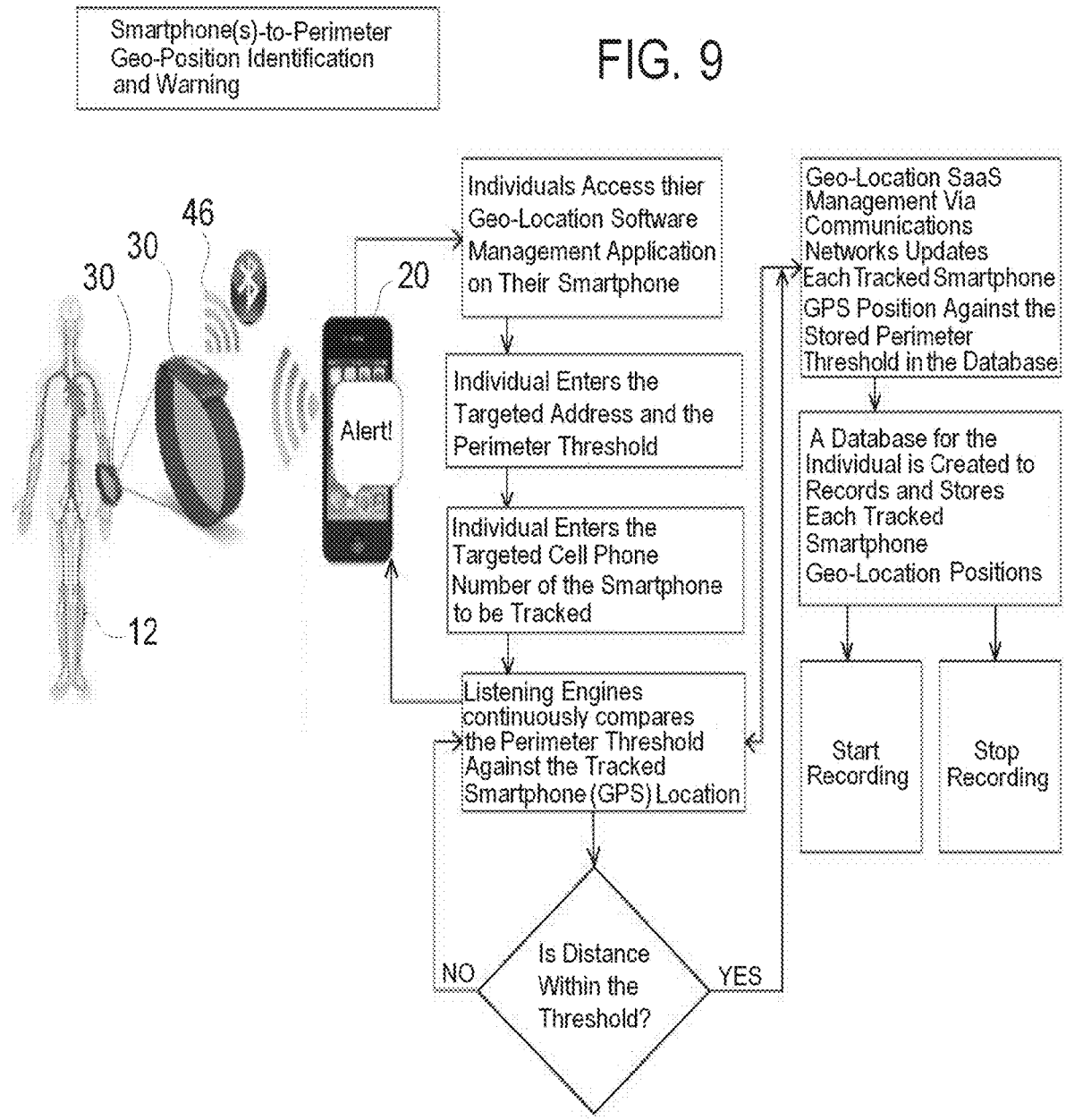
FIG. 9 is a schematic diagram of a process for communication of Smartphone to perimeter geo-position identification and warning in accordance with one aspect of the system of FIG. 1.

Additionally, the present invention system 10, as shown in FIG. 9, deals with smartphones-to-perimeter tracking. The process deals with the tracking of several individuals 12 using their smartphone cell numbers (GPS) position.

As defined above a smartphone 20 is a hand carried personal computer with a mobile operating system with the capabilities of a cell phone. Smartphones are typically pocket-sized hand held devices, but not exclusively. One category or subset of smartphones is a wrist based smartphone, sometimes called a smartwatch. Wrist based communication devices have held a long fascination with the United States public dating back to at least Jan. 13, 1946, with the appearance of the 2-Way Wrist Radio in a Dick Tracy comic which became one of the strip's most immediately recognizable icons. By the end of 2013 there were at least three commercial smartwatches incorporating smartphone technology including Samsung Galaxy Gear, Sony SmartWatch 2, and the Qualcomm Toq. The most well-known smartwatch was the Apple Watch announced in 2014. The present invention can be implemented with the smartphone 20 being a smartwatch with smartphone capabilities. Additionally, it is anticipated that such a system could further integrate the wristband 30 and the smartphone 20 into a single integrated component. The integrated smartwatch (smartphone 20) and bracelet 30 yields a far easier implemented system and prevents the phone 20 from being removed from the wristband 30, however the operation of the system would remain the same in such an integrated system. As a handheld smartphone 20 is more common than a wrist mounted smart watch type smartphone 20, the system is generally described herein in connection with the handheld version of the smartphone 20.

For the sake of clarification the following is a representative example to illustrate the utility of the system 10, in this case: Parents who would like to make sure that their kids do not leave the perimeter of a certain address, namely a school's address. The parents using the geo-location software management that is installed on their child's smartphone 20 (or the smartphone 20 that the child uses as the child 12 does not own the smartphone 20 in this case) can select the address of the school and set a threshold, which is a specific geo-location perimeter and radius. The parents also key in their kids' smartphone numbers to be tracked in the geo-location software management database located at 42. With the Child 12 wearing the bracelet 30, the moment the threshold of the tracked smartphones 20 exceeds the stored threshold, a warning is send to the parent's smartphone that is running the geo-location software management service. A warning can also be sent to the parents if the phone 20 is distanced from the bracelet 30 beyond a threshold distance (which has both phone theft or loss prevention aspects and prevents the child from thwarting the desired tracking) or if the bracelet is no longer identifying the unique ECG's of the child 12 (which feature will yield both medical safety aspects and compliance aspects for the parent).

Figure 10:
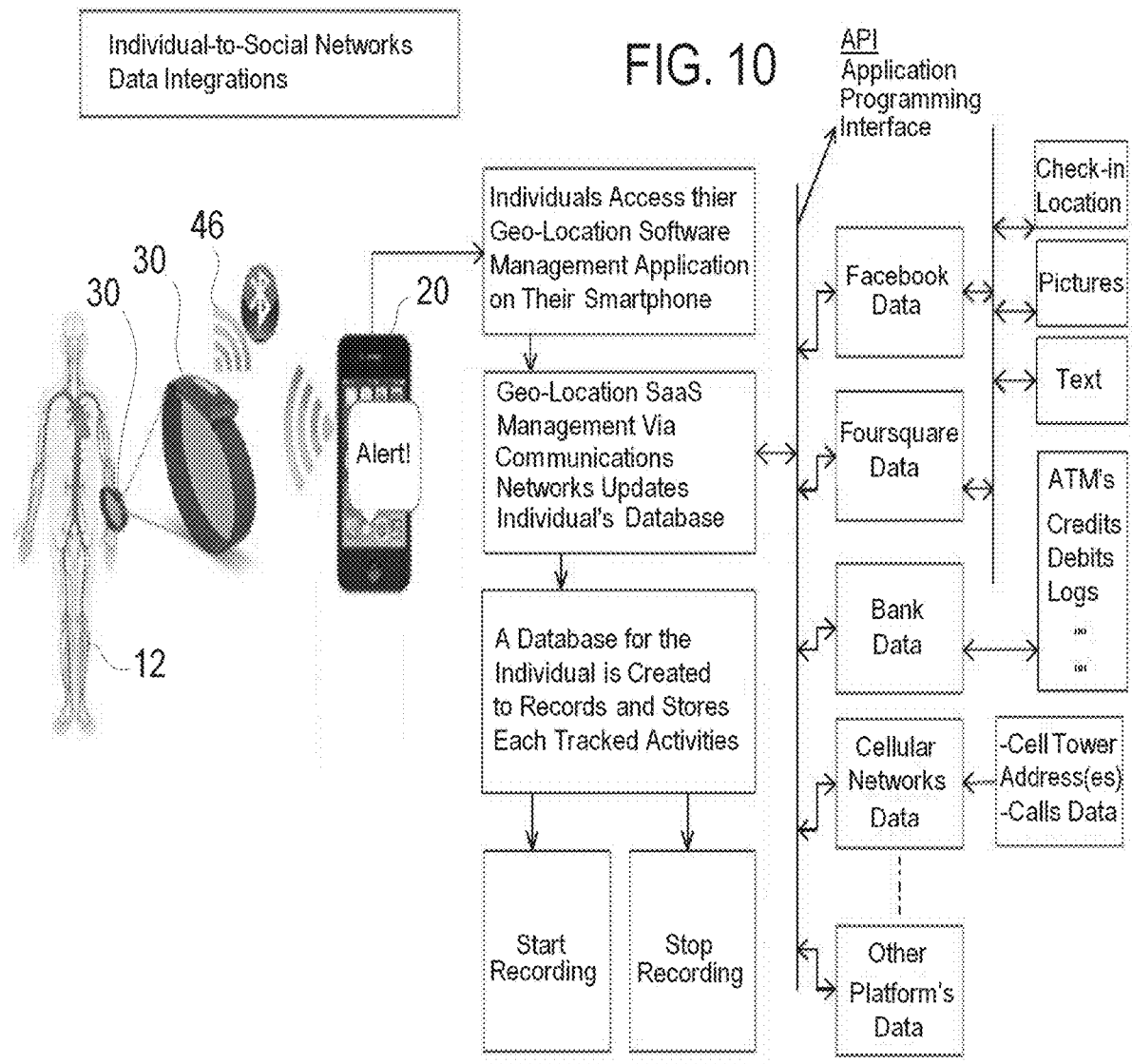
FIG. 10 is a schematic diagram of a process for Individual to social networks data integrations in accordance with one aspect of the system of FIG. 1.

The present system 10 also allows individuals 12 to access the geo-location software service that is running on their smartphones and activate the application programming interface (API) to automatically allowing other social network(s) location based check-ins software platforms data to be added and integrated to the individual's geo-location software management database, as generally shown in FIG. 10. Other platforms' data may be such as FACEBOOK® location base check-in data, FOURSQUARE® location base check-in data. The present system 10's API integration of social networks location base to the geo-location software management service is not limited to just FACEBOOK® and FOURSQUARE® data integration. The term check-in data in this present invention is not limited to only the time and the location base check-ins but also includes the pictures posted at the time of the check-ins as well as the embedded date, time stamp and the geo-location associated with each picture as well as the text message associated with the check-in message data.

Consider for example a work collaboration website that allows input from authorized users, and the present system can allow and manage inputs via user's phones 20 into the website from only authorized and verified users 12. For example, a news media outlet can allow reporters, photographers and/or editors as users 12 to upload and add verified managed content from their phones 20 to the media outlet webpage. In this era of "fake news" the added verification of the system 10 can become critical for news media outlets and social media outlets.

Social media platforms can utilize the system 10 to prevent anonymous or falsely attributed postings, minimizing the occurrence of "fake news" and providing for accountability for any such postings. The system 10 allows for managing of such inputs as well. Consider a University associated social platform that can assure that posting or commenting users 12 are in fact associated with the university and authorized to do so and can add the requisite information to a post automatically, such as adding "John Doe, 2006 alumni BS Electrical Engineering, commented on the Engineering Departments Grant Announcement:" to an authorized comment from John Doe. The tagging of postings and the amount of detail provided in such tags is easily modified by the administrators and likely allowed to be modified by the user 12 themselves, as known in the art. The present system 10 merely provides a seamless method of user authentication, including adding geo-authentication aspects. Consider again the University associated social platform and a section relating to comments relating to, for example, a University art exhibit, the system allows for system control or management to receive inputs only from authorized users 12 who are in a designated geo-location, thus only authorized users 12 who are in the vicinity of the art show (during times it is viewable) can post their reviews (or simply verify that they have in fact viewed the requisite show).

The present system 10 allows individuals 12 to access the geo-location software service 42 that is running on their smartphones 20 and activate the application programming interface (API), see FIG. 10, to automatically allow the individual's bank transaction(s) data to be added and integrated to the individual's geo-location software management database. The system 10 allows individuals 12 to access the geo-location software service 42 that is running on their smartphones 20 and activate the application programming interface (API), again shown in FIG. 10, to automatically allow the individual's wireless communication data to be added and integrated to the individual's geo-location software management database. Wireless communication data is not limited to the individual's cellphone data, but also includes the location region and or address of the cellphone towers where the calls and data communications came from.

Figure 11:
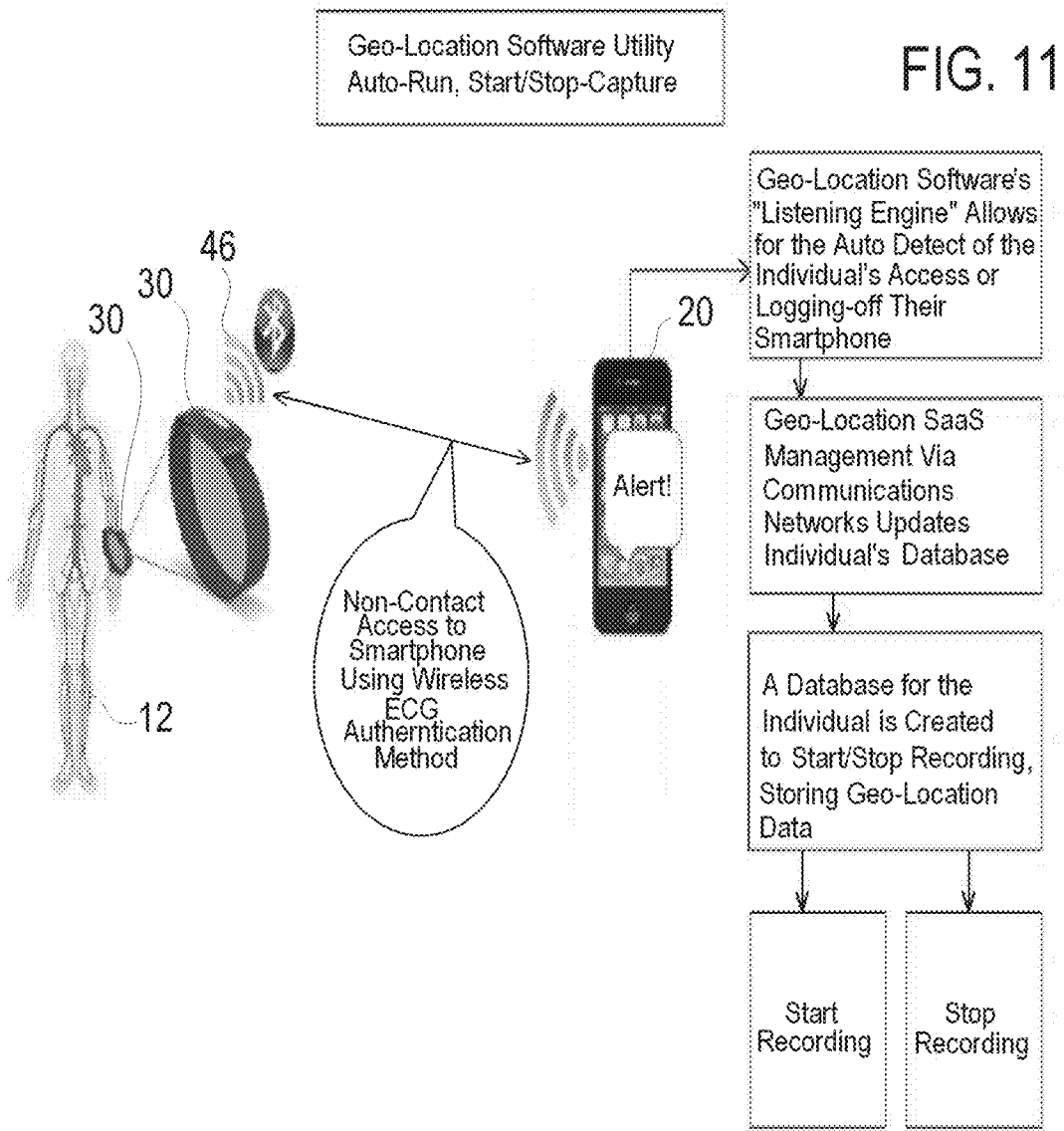
FIG. 11 is a schematic diagram of aspects of the geo-location software utility in accordance with one aspect of the system of FIG. 1.
Figure 12:
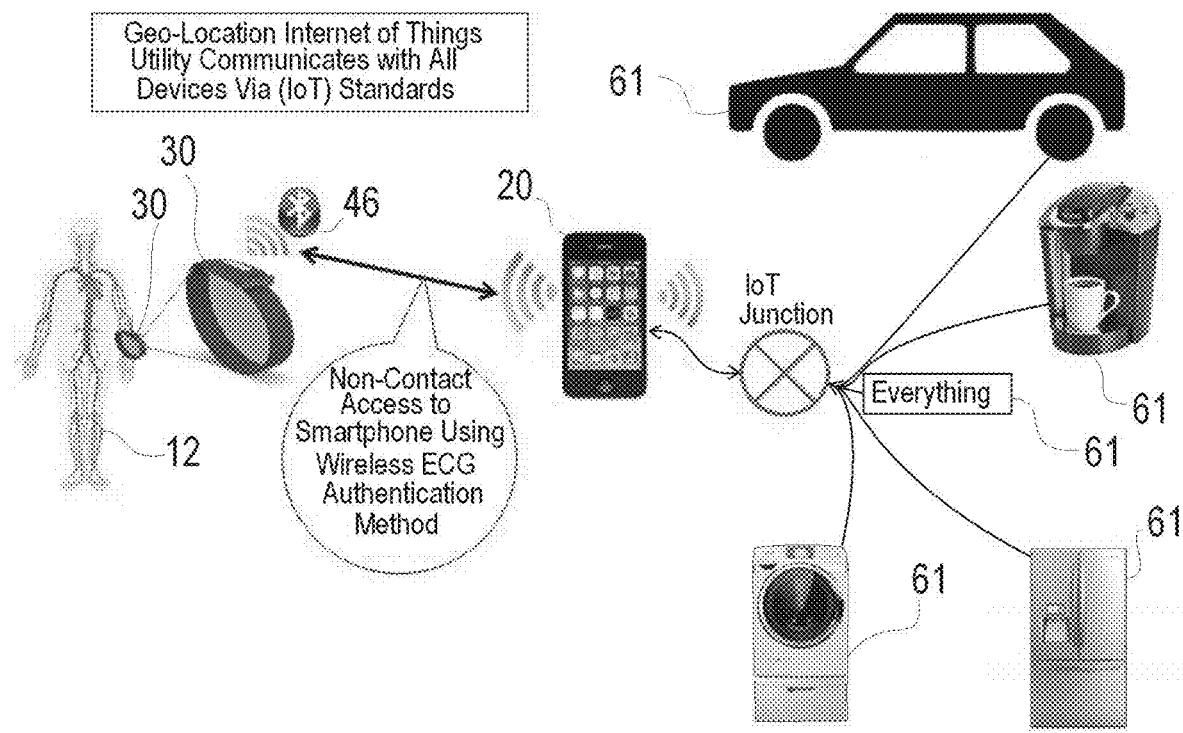
FIG. 12 is a schematic diagram of aspects of a geo-location internet of things utility in accordance with one aspect of the system of FIG. 1.

The present invention system 10 allows individuals 12 with the use of a wrist band 30's heart signal ECG based identification signature method to wirelessly and without the individual touching their smartphone to automatically authenticate and access their smartphone 20 allowing at that specific access instance for the geo-location software management service to automatically start capturing and recording the individual's smartphone geo-location (GPS) position data, see generally FIG. 11. Furthermore the present system 10 allows individuals 12 with the use of the wrist band 30 to enable the Internet-of-Things (IoT) devices 61 to identify the individual 12 who has authenticated to the IoT device(s) 61, shown in FIG. 12. The geo-location software utility 42 will register and retrieve data from the associated device 61: Data which is not limited to the Internet protocol (IP) of the devices and may be associated with address location, time of interaction(s) with the device, etc. Examples of such devices 61 can be a car, washing machines, refrigerator, TV, coffee maker, smart bulb. As a brief representative example, an apartment building may, as a safety concern, only allow interaction and operation with a washing machine or dryer with an authenticated user 12 when the user is located close to the device (e.g. in the building, on the same floor, etc), and the system 10 easily accommodates this application for the building manager. Note further billing for use of the interaction with the device 61 by the authenticating user can be handled/verified with the system 10 replacing the complex coin operated and related systems now in place. As a further example, parental control of TVs, Refrigerators and other smart devices 61 is easily implemented with the system 10 and the system 10 allows the device 61 to submit relevant information to the system 10 regarding the particulars of the interaction that can be relevant for the parent. The uses of smart devices 61 are legion and the present system 10 adds a simple cost effective individual and geographic verification aspect to the implementation of such devices 61, and further the information obtained from such devices 61 associated with authorized interaction and control of such devices 61 further enhances the applications of the system 10.

The present system 10 and associated method can be described or summarized as a comprehensive web3.0 software utility, an Internet of Things (IoT) geo-locations software management utility 42 to manage the individual 12's geo-location of their traveled path via biometric user identification coupled with capturing, recording and storing their smartphone 20's GPS location via a communications network 14. The individual 12 can access online via their smartphone 12 (or a desktop computer) the geo-location software utility to view and print the history of their traveled path. The present invention integrates the use of a biometric ECG wristband 30 that integrates a wireless heart rhythm (ECG) identification signature transmitter and allows for a wireless authentication of the individual 12 to access their smartphone 20. The present system 10 includes a process which starts automatically at the instance it detects that the individual 12 has gained access to their smartphone 20 and begins capturing and recording the individual's authenticated smartphone geo-location (GPS) position data. The individual's captured data includes the geo-location position of their smartphone's (GPS) position and the time it was captured. More particularly, the present invention deals with securing that both the individual 12 and the smartphone 20 are always present at the same geo-location at the time the geo-location of the smartphone via (GPS) position is captured and logged-in into the software as a service 42 database via a communications network 14. The present system 10 secures that the individual 12, and possible owner of the smartphone 20, is the unique user/owner of the smartphone 20 with the use the individual's cardiac rhythm ECG like a fingerprint signature to authenticate and gain access to the smartphone 20.

The above description is in the abstract but some representative examples may further highlight the applications for the system 10.

Fleet and Crew GPS Tracking

One implementation of the system 10 and associated method of the present invention is for what is known as GPS Fleet Tracking in which a company which operates a number of vehicles and drivers (e.g., for deliveries/pickups) desires to utilize GPS trackers for vehicle and driver management. Implementing existing GPS fleet tracking is known to reduce fuel costs by tracking driver behaviors that can drive fuel bills up and single out fuel charges by vehicle and eliminate unauthorized fuel-ups; and is known to potentially lower insurance premiums by allowing the entity to proactively manage and encourage driver safety; and is known to yield automatic governmental compliance with digital logbooks because the entity will obtain real time status information (e.g. HOS status) in the office and send proactive alerts to drivers to help prevent violations. As examples of conventional GPS Fleet Tracking systems see Fleetmatics Development Limited's FLEETMATICS™ system and Verizon's NETWORKFLEET™ system.

The system 10 of the present invention described above is easily operable as a cost effective GPS Fleet Tracking system and the current system 10 yields the additional benefits (above conventional GPS Fleet Tracking) of authenticating and tracking each individual 12 driver and/or crew member via their own smartphone 20. This system 10 also allows for tracking of a single driver 12 with multiple vehicles and individual crew members 12 even in interchanging crews (e.g. a crew member begins a shift with one vehicle and switches to a second or third vehicle throughout the shift). The vehicles may themselves, in some cases, be devices 61 that interact with the system 10 to give further detailed information regarding each individual's use of the vehicle (in addition to the identity and position data of the phone 20). However, one significant use of the system 10 is for inexpensive fleet tracking without retrofitting an existing vehicle fleet.

Legal System Individual Location Verification

1. Restraining Orders

Several distinct but related implementations of the system 10 and associated method of the present invention are presented in the legal system which has reason to verify and track the location of select individuals 12. One implementation is often found in the area of restraining orders, also known as protective orders that are common in family law. Alleged violations of restraining orders can clog the court process and cost the parties substantial sums in excess attorney fees as proof of violation or non-violation is difficult. The system 10 of the present invention can easily provide a provable court record of an individual 12 location when associated with their cell phone 20. Restrictions on coming close to another party's home, or place of business is easily implemented. Further, the system 10 allows the restriction and warnings to be expanded to a zone around select third party cell phones to be added. Warnings can be sent to the individual and the court and the other parties in the case. Further periods when the user does not have a verified location can be noted by the system. Voluntary adoption of the system 10 by users will likely be driven by the reduced legal fees.

2. Bail

The system 10 can be used by a court to inexpensively and effectively enforce bail restrictions on an individual 12 in criminal matters and thus allow far greater number of individuals qualify for bail and greatly reduce the cost of housing suspects awaiting trial. Geographic restrictions can be easily added for any individual 12 (e.g. prohibitions on leaving the state, prohibitions on going to certain locations). Restrictions on coming into contact with certain parties (e.g., witnesses, alleged victims) can easily be added via telephone numbers of the third parties and associated thresholds (with such numbers being withheld from the individual 12). Compliance with the system 10 is likely another condition of bail (e.g. an individual is advised "you must have your phone on at all times and also have the wristband 30 on so the system can track you"). Again voluntary adoption of the system 10 by individuals 12 will likely be driven by the reduced bail fees associated with adopting and complying with the system 10.

3. Parole/House Arrest Enforcement

The system 10 can be used by a court to inexpensively and effectively enforce parole and/or house arrest restrictions on an individual 12 in criminal matters and thus allow far greater number of individuals qualify for an automated supervised parole or house arrest and greatly reduce the costs to the criminal justice system. The system 10 is easily modified for individual parolees and or house arrest individuals. It can verify that they are at work during scheduled work days and at home when scheduled to be at home with alerts. Geographic restrictions and third party restrictions can also be added and monitored automatically. Warnings and or violations of the conditions or compliance can be sent to the individual and the court (e.g., the parole officer). The system 10 is cost effective and efficient.

Geographic Validation of Smartphone Captured Data

The system 10 for authenticating an individual 12's geo-location via a communication network 12 may include marking recordings, such as pictures, videos or audio recordings, taken with the individual's smartphone 20 with the geo-location where the image was taken, the time the image was taken, and the authenticated geo-location data of the individual 12 when and where the image was taken. The system 10 will allow for authentication of any image, video, audio recording and/or sensor reading recorded by the smartphone to verify the location and individual making the record via the smartphone. In this implementation of the invention a finger scan can be used as a passive biometric authentication technology.

1. Inspection-Inspector Authentication

Inspectors, such as building inspectors, will often obtain images or video (or even sensor readings) of the inspection to supplement the inspection. Sometimes it is questioned whether an image or video was taken at a given time, and/or taken by a given inspector at that time. The system 10 verifies the authorized individual 12 was with the phone 20 when the subject recording was taken and the data is stamped (also called an electronic watermark) on the recording. The system 10 thus validates the inspection, and as noted above In this implementation of the invention a finger scan can be used as a passive biometric authentication technology.

2. Photographer—Copyright Owner

A copyright in an image or video will vest when the image is fixed in tangible form (when the image is taken) and the ownership will vest in the author (e.g. the photographer), outside of a work made for hire. Actually in a work made for hire situation the present invention is also particularly helpful in that the system verifies that the subject work was made during work hours by the creators who was hired at the designated location. A timely image of a current event can be a valuable commodity for the author (photographer) and purchasers sometimes need some assurance that the person proffering authorship and ownership of the work in question actually holds title thereto or are authorized to post on a given site. The system 10 verifies the authorized individual 12 was with the phone 20 when the subject recording was taken and the image/video is stamped (also called an electronic watermark) on the recording, thus the system 10 corroborates ownership of the work in question, and again in this implementation of the invention a finger scan can be used as a passive biometric authentication technology. Recording this material onto a blockchain as detailed below creates an NFT with the integrated creator authentication.

3. Research-Researcher Authentication

Smartphones 20 can take almost an unlimited type of data as any number of sensors have been designed to couple to a portable phone 20. The system 10 allows a simple inexpensive method for researchers to validate the time, place and person obtaining the data by electronic watermarking the recordings with the relevant information. Questions regarding timing or validity of the data (or who obtained such data), which can needlessly question the veracity of a test, are simply removed with implementation of the system 10. Arguably the system 10 can be part of a researcher's best practices, and in this implementation of the invention a finger scan can be used as a passive biometric authentication technology when integrated into sensor activation. As noted above with UC Berkeley's NFTs for two Nobel Prize-winning invention disclosures (CRISPR-Cas9 gene editing and cancer immunotherapy) such material can be collectable and commercial. Additionally such research NFT's could provide indisputable proof of inventorship and FDA product or drug development history files.

Geographic Limits for App Access

As described above the system 10 can be used to give the user access to operation of the cell phone 20 completely. The system may also be used to restrict access to only a portion of the cell phone apps (i.e. a third party may use the phone 20 but some apps will be locked out because there is no verification of identity.) However the present system 10 can go further than merely limiting access to certain applications, the system 10 can tie the access the further requirement of the phone 20 and the verified user 12 being in a designated location. For example an employer can give a user 12 a phone 20 with select apps that are only accessible at the office by the user 12. This aspect can be important for NFT creation that assures the company is the proper owner of the created material.

1. Financial Services Authentication—Bank ATM, on-Line Banking and Credit Cards

One application for geographic limits for application access is interaction financial services authentication such as with bank ATMs. In the ATM environment, the system 10 will verify the identity of the individual 12 via the biometric ECG band (or other biometric identification technology) to add an initial layer of security, but will also verify that the individual and the phone are in close proximity to the designated ATM to add a further layer of security difficult to defeat.

The ATM is merely a representative example in the banking field as the system 10 is adopted for fighting bank fraud in general. Mobile banking on smartphones 20 and other devices is increasing, as is the issues with bank fraud. The present system 10 used with mobile apps is again hard to defeat, even if someone takes the smartphone 20 and knows the passwords to the online banking accounts. The mobile banking app used in conjunction with the present system may be on the smartphone 20 or on a separate device like a laptop or a desktop, but use of the system 10 for user authentication for these financial services adds a layer of simple biometric security that banking customers may pay a significant premium to enjoy. In this implementation of the invention a finger scan can be used as a passive biometric authentication technology when the scan is integrated with a transaction authorization or the like.

ATM card usage is analogous to credit card usage, and credit card fraud is estimated to exceed $35 billion dollars in 2020. The present system can be associated with credit card usage to verify the users and substantially eliminate fraud on cards tied to the system 10.

2. Phone Applications that an Individual can Only Access at a Designated Location It may be desirable to allow individuals to have simple access to and interact with "on-site systems", such as hospital employees accessing patient records at a hospital, through the individuals phone, and to automatically prevent such access when the individuals leave a designated area (e.g. when the individual hospital employee leaves the hospital). The system 10 allows this functionality to be easily implemented and improve employee's ability to cost effectively interact with secure records in a desired and secure manner.

3. Devices that an Individual can Only Access at a Designated Location

It may be desirable to allow authenticated individuals to have access to and interact with on-site devices 61, such as a worksite washing machine, through the individuals phone 20, and to automatically prevent such access when the individual leaves a designated area (e.g. when the individual employee leaves the workplace). The system 10 provides for authenticating the user 12 via the communications network for interaction of the individual user with these Internet-Of-Things devices 61. The system 10 allows this functionality to be easily implemented and improve employee's ability to cost effectively interact with an onsite device 61 in a desired and controlled manner. The device 61 can communicate information to the system 10 relevant to the individual's interaction with the device 61 sufficient for the efficient control of the resource/device 61 (e.g. finding out that the marketing department is using the coffee maker or copier or 3d printer or similar device 61 more than the engineering department and accounting department and human recourses combined and it warrants getting them their own device 61—and accounting for the device 61 accordingly for more efficient business management). A cooperative Laundromat (such as at an apartment building) using washing machine and dryers as devices 61, or a library using onsite resource devices 61 (copiers, printers, etc.) represent other obvious applications of the system 10 in this context. The system 10 can quickly and easily be updated with adding new authenticated persons 12 and deleting those no longer authorized in a relatively simple manner, making the system useful for settings in which personnel with access rapidly turns over, such as a University setting and Lab access. Further the devices 61 will have a record of the proof of presence of the specific user that will even stand up in court. In this implementation of the invention a finger scan can be used as a passive biometric authentication technology when the scan is integrated into the device 61 interaction on the app of the phone 20 of the user 12.

Transportation

The system 10 can be implemented to verify users at variable locations, such as would be practical for Uber and Lift (both for real time verifying of both passengers and drivers) or TAA applications. For example, prescreened users of the system 10 can be granted expedited security protocols through TAA as an improved supplement to an existing program of TA. In this implementation of the invention a finger scan can be used as a passive biometric authentication technology when combined with other interaction, such as a verification made by the user 12 during the screening (e.g. "Press here to verify that you are not carrying the following materials . . . ").

Parental Supervision

Most of the above applications can have separate utility for parents supervising their children as the users 12 and their children's use of phones 20.

Blockchain Applications

The present invention defines a systems and method of a communications network, a private blockchain network and a token issuance schema that grants access to the private blockchain network' data-as-a-service. The blockchain application or implementation is critical in the NFT creation aspects of the present invention.

Figure 13:
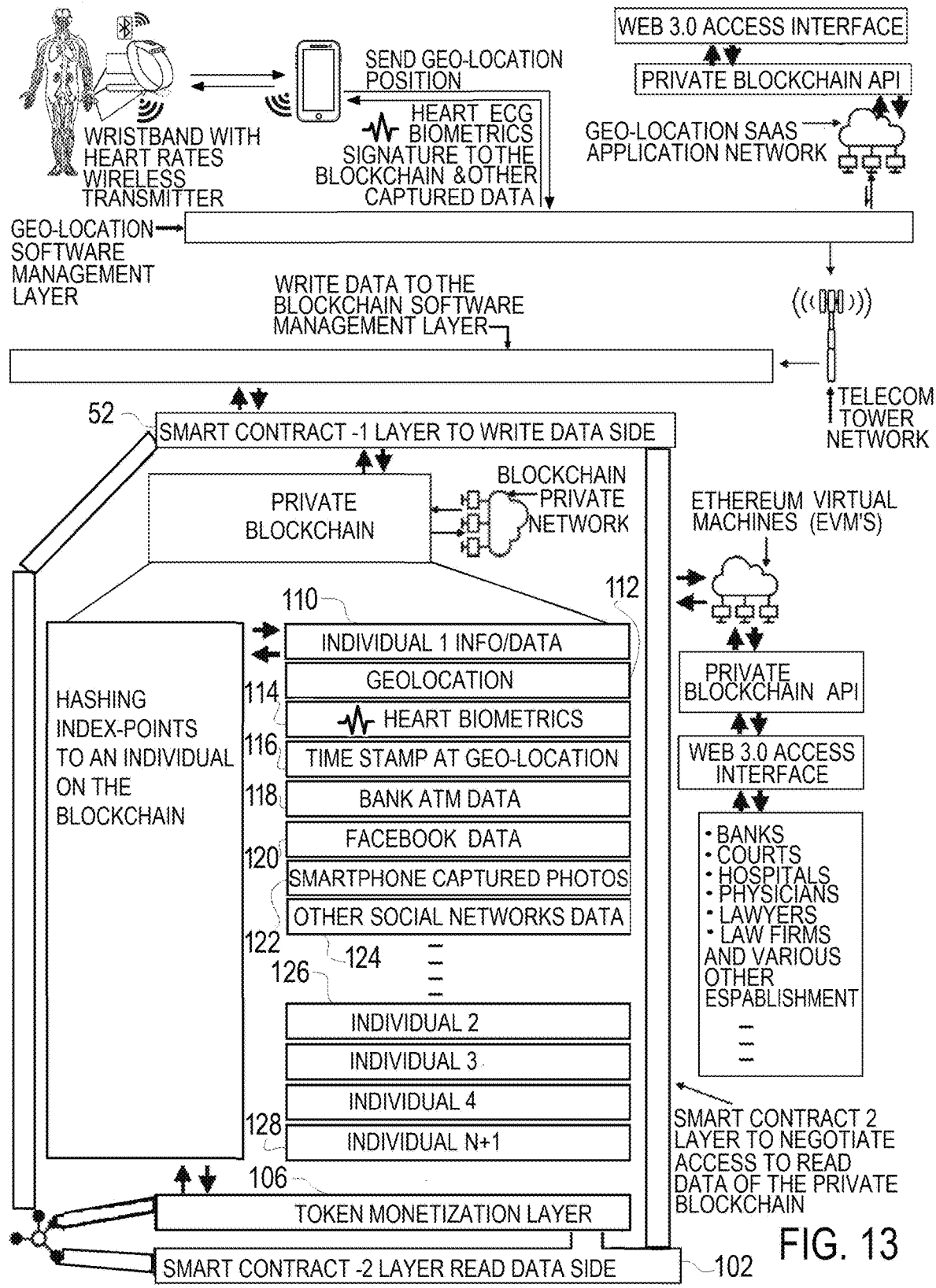
FIG. 13 is a schematic diagram of a Private Blockchain incorporating an individual's authenticated geo-locations data in accordance with one aspect of the present invention.

This invention is directed to a cost effective, efficient, system 10 see figure-13 for a write-a private blockchain network 20 to write-to and read-from the individual's authenticated data 20, smart contracts 52 issuing a token 106 to consume as-a-service the goods and services of the stored hashes of the on-chain of the geo-location data in 110, 112,114, 116,118,120, 122, 124, 126 and the actual data 10, 112,114, 116,118,120, 122, 124, 126 on the private blockchain network 20 associated with the individual's smartphone 12, which includes a GPS receiving into the blockchain 20 the hashes of the geo-location authenticated data in 110, 112,114, 116,118,120, 122, 124, 126 of each individual 12 via a communication network, a private blockchain network 20.

Figure 2:
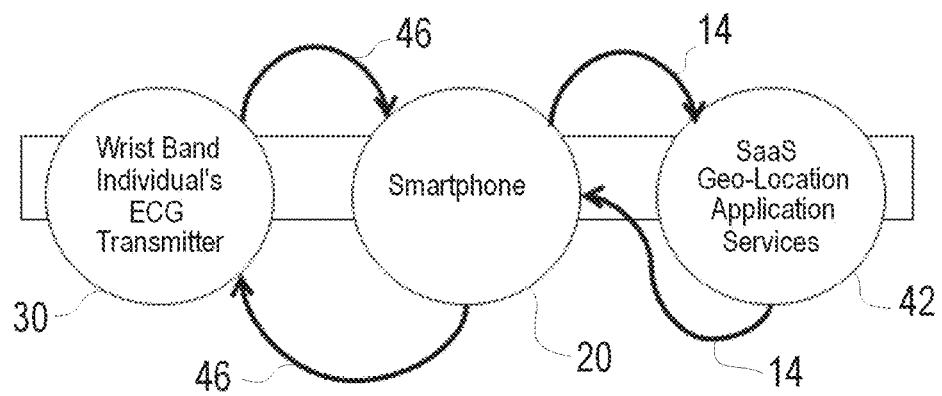
FIG. 2 is a schematic diagram of an individual to smartphone distance management layer of the system of FIG. 1.
Figure 3:
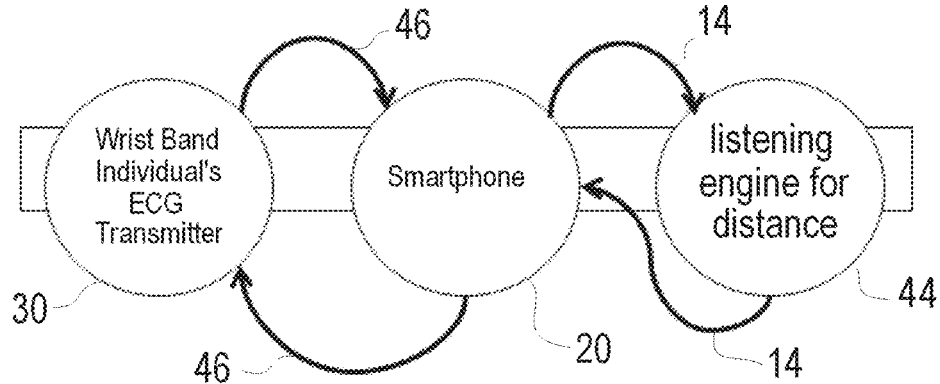
FIG. 3 is a schematic diagram of a ECG signal ID management layer of the system of FIG. 1.
Figure 4:
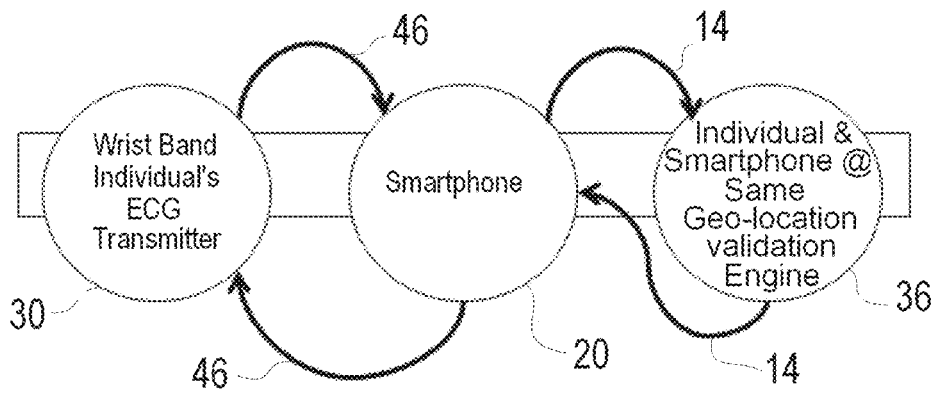
FIG. 4 is a schematic diagram of a geo-location application login session management layer of the system of FIG. 1.
Figure 5:
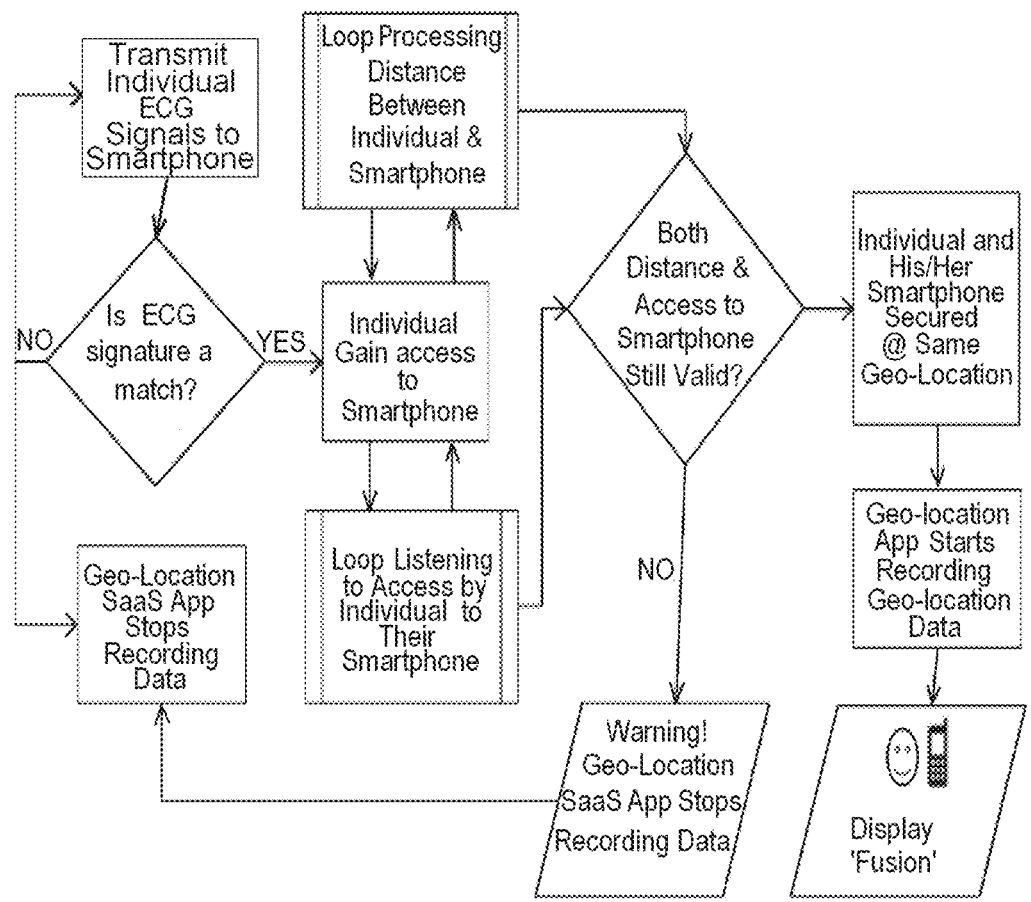
FIG. 5 is a schematic diagram of a process for verifying the same location of the individual and their smartphone of the system of FIG. 1.
Figure 6:
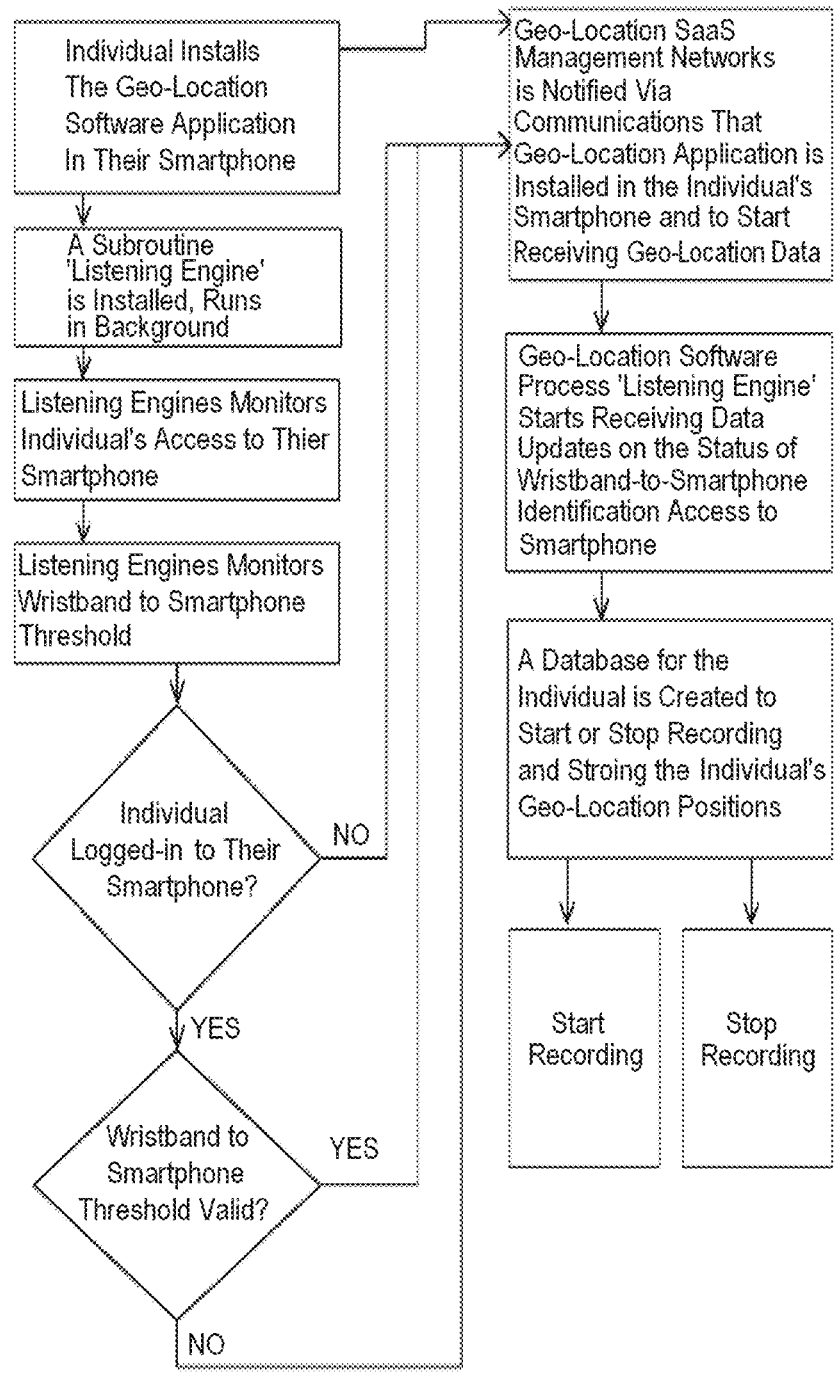
FIG. 6 is a schematic diagram of a process for communication between an individual's smartphone geo-location utility and geo-location Saas networks of the system of FIG. 1.

This invention is directed to a cost effective digital rights management (DRM), efficient on the blockchain monetization of the stored geolocation authenticated photo(s) data records of the individual who actually captured the photo 122 via smartphone 12 while wearing the wristband, system 10 see figure-1 and FIG. 2 for private blockchain network 20 to read-from the blockchain an individual's authenticated profile records data 20 in this case the history records of the captured photo, photos 122, place picture was taken, time the picture was taken all negotiated through swarm executed via a read-from the blockchain 20, with access arbitration via smart contracts 52, for granted access issued in tokens 106.

FIG. 13 demonstrates that the present invention is directed to a cost effective, efficient incorporation into a blockchain data storage and security. Blockchain presents a number of challenges to all establishment not least of which is the fundamental difference between programming for a shared virtual computer versus, say, some high-powered machine. One of the challenges of working with this platform is data storage. The only obstacle is the astronomical costs associated with storing data on the Ethereal blockchain networks 20. Generally the cost to store data such as 110, 112, 114, 116,118,120, 122, 124, 126 on the Ethereum blockchain can be prohibitive, for example storing 1 GB would require 32 000 Ether a cost of around $20 000 0001 Therefore, the present invention resorts to storing the bulk data 110, 112, 114, 116, 118,120, 122, 124, 126 off-chain on the "cloud" via Swarm and hashes of the data on-chain, allowing users to easily verify the integrity of the data without actually paying the massive costs of storing on the blockchain itself. This invention is directed to a cost effective, efficient, system 10 incorporated into a private blockchain Dapp instance running web 3.0 18.

The present application or system has many advantages and uses only some of which are touched on above. The system 10 may be implemented into the business logic that governs the process of In-App Purchasing, especially Subscription Management, AppStore receipt validation and finally a batch treatment or a program that runs automatically on each subscription expiration date to check the renewal of the subscription (payment). The present invention contemplates the integration into the system 10 solution (in server side: Database, Business logic and web API) of elements such as Sales management and Business Intelligence (BI), which is a technology-driven process for analyzing data and presenting actionable information to help executives, managers and other corporate end users, make informed business decisions.

The present invention yields, as discussed above a passive geolocation authentication utility interfaces via an API with FACEBOOK, INSTAGRAM, FOURSQUARE, YELP and other social media. Alternatively the system 10 provides in some implementations a passive image geoauthentication using a fingerprint button that both scans for fingerprint and takes image, the image is geo-watermarked with option through an (API) to choose to store watermarked image into a person's profile in the geoauthentication utility itself, INSTAGRAM, FACEBOOK, YELP, FOURSQUARE and other social media using one click. The system 10, as described above can provide a passive/face-id image geoauthentication using face-id, wherein the image is geo-watermarked with option select through an (API) to store watermarked image into a person's profile on INSTAGRAM, FACEBOOK, YELP, FOURSQUARE and other social media using one click. The system 10 may provide a passive geoauthentication using fingerprint button to check into places using geoauthentication software management utility, the geoauthenticated check in to a place with option select through an (API) to add and store the verified check in into a person's social media profile on INSTAGRAM, FACEBOOK, YELP, FOURSQUARE and other social media using one click. The system 10 can yield a passive/face-id geoauthentication using face-id to check into places using geoauthentication software management utility. The geoauthenticated check in to a place may further include an option to select through an api to add and store the verified check into a place in a person's social media profile on INSTAGRAM, FACEBOOK, YELP, FOURSQUARE and other social media using one click. The system 10 overcomes the fake/false check-ins and postings that is taking place in social media and to INSTAGRAM, SNAPCHAT, FACEBOOK in particular. The system 10 can add a verification or authentication message, such as "a verified you!" to all image/video postings and check-ins into locations when using social media.

5G

Another aspect of the present invention is tethering the individual's ECG and owner of the smartphone to their smartphone and to their geo-location via the smartphone GPS and to the IoT device's geographical physical location provided by IPv6 base network and the integrated GPS/Cell within the IoT devices. This structure allows for now adding the 4th identifier which is the IoT devices powered by the integrated GPS/Cell and IPv6 mac address. One feature of the present invention provides a method for encoding geolocation information into a next-generation internet protocol (IP) address, such as IPv6, to facilitate distribution of geolocation information among networked devices. A request for an IP address assignment is received from a network device. The geographical location for the network device is obtained. An IP address is assigned or generated that includes the geographical location. The assigned IP address is then provided to the network device. By encoding the geolocation information of a first network device into the IP address assigned to the first network device, other network devices are able to readily obtain the geographical location of the first network device. This method propagates geolocation information for network devices as part of the IP address, thus avoiding the need for separate geolocation distribution messaging. As the network device moves, its IP address is changed to update its geographical location information. The present invention can verify via the IPv6 communications network the biometric user identification technology is within a preset proximity to the smartphone to authenticate the individual's mobile geo-location anywhere within a geographic scope of the communications network of the smartphone, and further including the step limiting access to at least some of the smartphone applications to the individual as verified by the biometric user identification technology.

NFTS

The above described Method and Apparatus for Passive Authentication of an Individual's Geo-Location Via a Communication Network and for User Authenticating Images, Video, Data, Social Media Content and applications on the blockchain represent creating unique digital assets or Non-Fungible Token (NFT). As noted above a non-fungible asset (NFT) is a type of cryptographic token on a blockchain that represents a single asset. These can be fully digital assets or tokenized versions of real world assets. Since NFTs are not interchangeable with each other, they can function as proof of authenticity and ownership within the digital realm. Fungible means that the individual units of an asset are interchangeable and essentially indistinguishable from one another. For example, fiat currencies are fungible, because each unit is exchangeable for any other equivalent individual unit. A ten-dollar bill is interchangeable with any other ten-dollar bill that is authentic.

First of all, if one desires want to turn a piece of artwork into an NFT it's very important that you are the creator and owner of the piece. Creating your own NFT artwork is a relatively simple process and doesn't require complex knowledge of the crypto industry. Before you start work, you will need to decide on which blockchain you want to issue your NFTs to. Ethereum is currently the leading blockchain service for NFT issuance other blockchain platforms are available and can be implemented. A non-fungible token is a unit of data stored on a digital ledger, called a blockchain that certifies a digital asset to be unique and therefore not interchangeable. NFTs can be used to represent items such as photos, videos, audio, and other types of digital files.

Figure 14:
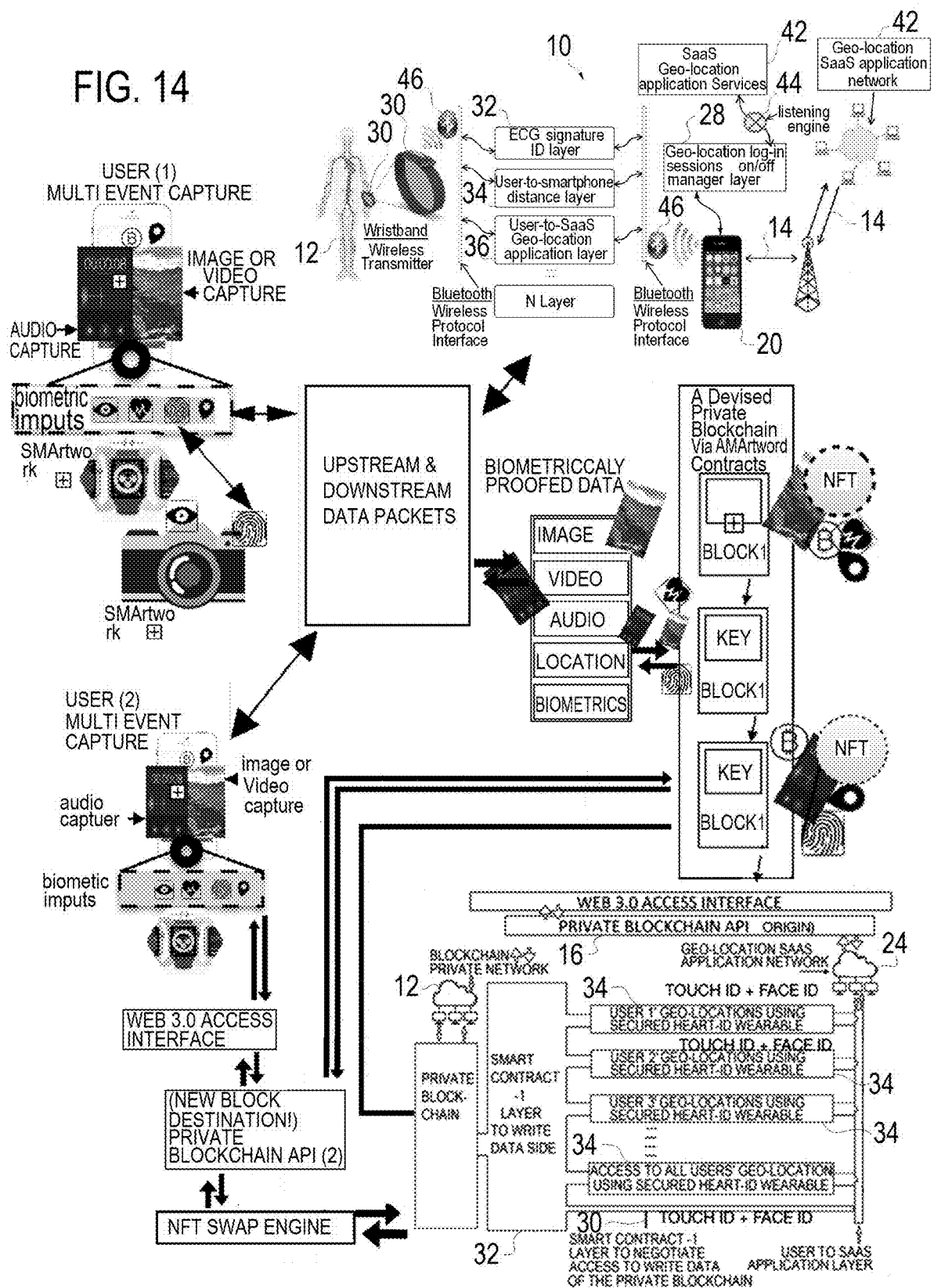
FIG. 14 is a schematic diagram of a cellular communication network based method of non-fungible token creation with integrated creator biometric authentication according to the present invention.

As detailed above the present invention provides a cellular communication network based method of non-fungible token creation with integrated creator biometric authentication comprising the steps of: a) providing the individual with a smartphone having a global positioning system (GPS) receiving unit associated with the communications network; b) providing the individual with a passive biometric user identification technology coupled to the smartphone; c) obtaining via the communications network the geo-location of the smartphone utilizing the GPS receiving unit; d) identifying the individual with the passive biometric user identification technology by passively obtaining biometric characteristics that are unique to each human via the communications network; e) identifying digital data files on the smartphone; f) verifying via the communications network the biometric user identification technology is within a preset proximity to the smartphone; g) authenticating the individual via the communications network and creating authentication data associated with the authenticated individual and associated with the digital data files; and h) recording on a blockchain the authentication data of the individual and authentication data associated with the digital data files. The biometric authentication and the issuance of the token as described above in the Authentication of an Individual's Geo-Location Via a Communication Network and for User Authenticating Images, video, data and Social Media Content and applications describes the unicity of each digital asset and its ownership linked via the user's biometrics to the individual as mentioned and described: The data stored on the blockchain or what's referred to as Digital Assets: The individual's unique biometric data, the individual's location data via GPS cellular location coordinates, the image the individual took, the video, the audio the individual took and social media and applications. The storing of Individual's authenticated data assets on the blockchain can be referred to by definition as digital assets, and the issuance of the token as mentioned above can be refried to as Non-fungible Token of (NFT). FIG. 14 is a schematic diagram of a cellular communication network based method of non-fungible token creation with integrated creator biometric authentication according to the present invention.

The one click to artwork conversion to its digital asset in the form of a Non-Fungible Token or NFT describes a process by which the individual's artwork and or assets: The individual's location, the biometrically authenticated Images, Video, data, audio and Social Media Content and applications who are then process and converted to digital asset on the blockchain and a Token is issued. In the invention when you turn an image into an NFT generally the artwork itself does not get stored in the Blockchain. Rather an entry in the blockchain gets created with the help of smart contracts and within its metadata only consists of a short description of the individual's biometrics unique ECG information, the individual's geo-location data, the image captured, the video captured, the audio captured and something as simple as a link that refers to a place in the web where the actuate artwork data is stored.

The One-Click process describes the method and system for an individual to biometrically authenticate at the instance of capturing their artwork and or assets (collectively digital data files) referred to here as the individual's location captured by the cellular GPS, the image taken, the video, and or the audio captured INTO authenticated digital assets (e.g. the digital files) wrapped around an issued token on the blockchain using only one-touch or one click of the smartphone capture button. FIG. 14 schematically illustrates the multi-event that takes place when the individual touches their smartphones button to capture their (artwork); the multi-event describes the: Capture of the artwork, the authentication of the artwork, the conversion of the artwork into asset into a digital asset, the issuance of a token to wrap the artwork into a NON-Fungible (NFT) all happening in one single instance; one single click or trigger and or activation of the smartphone capture button. The Multi-event describes the simultaneous capture of the artwork and the activation of the smartphone biometric finger scanner to perform the artwork capture, the artwork authentication simultaneously linking the artwork captured to the individual who took it; while at the same time, generating a token and wrapping the artwork captured and its related data around it into digital assets available on the blockchain. The One-Click process converting artwork into digital assets and into an (NFT) using a wearable enabled with ECG biometrics—As Described above is then used as the same process definition applied in the finger scan passive biometrics function to create an artwork (NFT). And the same One-Click process converting an Artwork into an (NFT) using Facial biometrics may be applied here.

The present invention provides the individual with a biometric user identification technology coupled to the smartphone; where the smartphone touch-id button, the touch-id button has a built-in fingerprint scanner mechanism, this fingerprint scanner mechanism is activated simultaneously during the click/touch button in a multi-event: to (1) take image and at the same time to scan the fingerprint biometrics of the individual. Therefore, the image is biometrically authenticated and has all the data authentication associated with it: Location, the individual's fingerprint, the date stamped and the image marker. The image is then recorded on the private blockchain with its associated authentication data and becomes a ONE-CLICK AUTHENTICATED-NFT. The same event and process takes place when providing the individual with an ECG biometric user identification technology coupled to the smartphone. The same event and process takes place when providing the individual with a Facial Identification/Iris based biometric user identification technology coupled to the smartphone It is apparent that many variations to the present invention may be made without departing from the spirit and scope of the invention. The present invention is defined by the appended claims and equivalents thereto.

What is claimed is:

1. A cellular communication network based method of non-fungible token creation with integrated creator biometric authentication comprising the steps of:
   a) providing an individual with a smartphone having a global positioning system (GPS) receiving unit associated with a cellular communications network for voice and data communication;
   b) providing the individual with a passive biometric user identification technology coupled to the smartphone;
   c) obtaining via the communications network a geo-location of the smartphone utilizing the GPS receiving unit;
   d) identifying the individual with the passive biometric user identification technology by passively obtaining biometric characteristics that are unique to each human via the communications network;
   e) identifying digital data files on the smartphone with a single user click; wherein the digital data files comprising the geo-location of the smartphone, the biometric characteristics, and at least one of audio, video, and image files;
   f) verifying via the communications network the biometric user identification technology is within a preset proximity to the smartphone;
   g) authenticating the individual via the communications network and creating authentication data comprising the digital data files; and
   h) recording on a blockchain the authentication data forming a non-fungible token.

2. The communication network based method of claim 1, wherein the biometric user identification technology utilizes the individual's electrocardiogram as a biometric characteristic that is unique to each human.

3. The communication network based method of claim 1, wherein the biometric user identification technology utilizes a wristband worn by the individual and wherein the wristband is coupled to the smartphone, and wherein the step of verifying via the communications network the biometric user identification technology is within a preset proximity to the smartphone to authenticate the individual's mobile geo-location anywhere within a geographic scope of the communications network of the smartphone.

4. The communication network based method of claim 1, wherein the step of recording the individual's authentication data includes the steps of recording the individual's authentication data off of the associated blockchain and recording hashes of the recorded data on the associated blockchain.

5. The communication network based method of claim 4, wherein the step of recording the individual's authentication data off of the associated blockchain is on the cloud.

6. The communication network based method of claim 5, wherein the digital data files include at least one of audio, video, and image files.

7. The communication network based method of claim 1 wherein the method includes authenticating multiple individuals, wherein each individual is provided with an individual smartphone and at least some individuals use a smartphone worn on a wrist.

8. The communication network based method of claim 7, wherein the method includes the step of incorporating defined restricted areas for each individual.

9. The communication network based method of claim 8, wherein the defined restricted areas for each user is configured to be able to be varied by time.

10. The communication network based method of claim 9, wherein the method includes the step of sending a warning message to a user when the user is approaching a boundary of the defined restricted area for that user.

11. The communication network based method of claim 1, further including the step of integrating the authentication data of the individual user with location based social networks data as proof-of-presence of the individual user in the location based social network data.

* * * * *